(12) United States Patent
Mande et al.

(10) Patent No.: US 8,972,200 B2
(45) Date of Patent: Mar. 3, 2015

(54) COMPRESSION OF GENOMIC DATA

(75) Inventors: Sharmila Shekhar Mande, Maharashtra (IN); Monzoorul Haque Mohammed, Andhra Pradesh (IN); Anirban Dutta, Maharashtra (IN); Tungadri Bose, Maharashtra (IN); Sudha Chadaram, Andhra Pradesh (IN)

(73) Assignee: Tata Consultancy Services Limited, Mumbai (IN)

( * ) Notice: Subject to any disclaimer, the term of this patent is extended or adjusted under 35 U.S.C. 154(b) by 259 days.

(21) Appl. No.: 13/428,790

(22) Filed: Mar. 23, 2012

(65) Prior Publication Data
US 2013/0132353 A1 May 23, 2013

(30) Foreign Application Priority Data
Nov. 18, 2011 (IN) .......................... 3254/MUM/2011

(51) Int. Cl.
*G06F 19/22* (2011.01)
(52) U.S. Cl.
CPC ...................................... *G06F 19/22* (2013.01)
USPC .......................................................... 702/19
(58) Field of Classification Search
None
See application file for complete search history.

(56) References Cited

U.S. PATENT DOCUMENTS

| | | | |
|---|---|---|---|
| 7,657,383 B2 * | 2/2010 | Allard et al. .................... | 702/20 |
| 2007/0282933 A1 | 12/2007 | Monro | |
| 2011/0295858 A1 * | 12/2011 | Ahn et al. ...................... | 707/741 |
| 2012/0089339 A1 * | 4/2012 | Ganeshalingam et al. ..... | 702/19 |
| 2012/0233202 A1 * | 9/2012 | Ganeshalingam et al. ... | 707/769 |
| 2012/0330567 A1 * | 12/2012 | Bauer et al. ..................... | 702/20 |
| 2013/0031092 A1 * | 1/2013 | Bhola et al. .................... | 707/737 |
| 2013/0204851 A1 * | 8/2013 | Bhola et al. .................... | 707/693 |

FOREIGN PATENT DOCUMENTS

| | | | |
|---|---|---|---|
| KR | 20130069427 | * | 6/2013 |
| WO | 2004/051863 A1 | | 6/2004 |
| WO | 2007/149358 A1 | | 12/2007 |

OTHER PUBLICATIONS

Bhola et al. (2011 IEEE International Conference on Bioinformatics and Biomedicine (BIBM Conference) Nov. 12-15, 2011, Atlanta, GA, USA).*
Brandon et al. (Bioinformatics (2009) vol. 25, No. 14, pp. 1731-1738).*
Fritz et al. (Genome Research (2011) Published online Jan. 18, 2011).*
Giancarlo et al. (Bioinformatics (2009) vol. 25, No. 13:1575-1586).*
Pinho et al. (PLoS ONE (2010) vol. 6, No. 6:e21588 (1-7).*
Tembe et al. (Bioinformatics (2010) vol. 26, No. 17:2192-2194.*
Hosang M, "A Character Elimination Algorithm for Lossless Data Compression", Data Compression Conference, Proceedings. DCC, Apr. 2, 2002, pp. 1-9, XP002246070, IEEE Computer Society Press, Los Alamitos, CA, US.
S. Deorowicz et al, Compression of DNA sequence reads in FASTQ format, Bioinformatics, Mar. 15, 2011, pp. 860-862, vol. 27, No. 6, XP0550771 00, ISSN: 1367-4803.
Batista L et al, "Text Pre-processing for Lossless Compression", Data Compression Conference, 2008. DCC 2008, IEEE, Piscataway, NJ, USA, Mar. 25, 2008 p. 506, XP031241212, ISBN: 978-0-7695-3121-2.
Anonymous, "Delta encoding", Oct. 27, 2011, XP055048430, Retrieved from the Internet: URL:http://en.wikipedia.org/w/index.php?title=Delta_encoding&oldid=457655719.
Giancarlo R et al, "Textual data compression in computational biology: A synopsis", Bioinformatics, Oxford University Press, Surrey, GB, vol. 25, No. 13, Jul. 1, 2009, pp. 1575-1586, XP002571 066, ISSN: 1367-4803.
Metzker ML., "Sequencing technologies—the next generation", 1.1. Nat Rev Genet. Jan. 2010;11(1):31-46.
Jun Zhang, Rod Chiodini, Ahmed Badr, Genfa Zhang, "The impact of next-generation sequencing on genomics", Journal of Genetics and Genomics, vol. 38, Issue 3, Mar. 20, 2011, pp. 95-109.
Cochrane G, Karsch-Mizrachi I, Nakamura Y; International Nucleotide Sequence Database Collaboration. Nucleic Acids Res. Jan. 2011;39(Database issue):D15-8.
Grumbach, S. and F. Tahi (1994). "A new challenge for compression algorithms: genetic sequences". Information Processing & Management 30(6), 875-886.
Rivals, E., J.-P. Delahaye, M. Dauchet, and O. Delgrange (1996). "A guaranteed compression scheme for repetitive DNA sequences." In Proc. of the Data Compression Conf., DCC-96, Snowbird, Utah, pp. 453.
Matsumoto, T., K. Sadakane, and H. Imai (2000). "Biological sequence compression algorithms." Genome Informatics 2000: Proc. of the 11th Workshop, Tokyo, Japan, pp. 43-52.
Chen, X., M. Li, B. Ma, and J. Tromp (2002). "DNACompress: fast and effective DNA sequence compression." Bioinformatics 18(12), 2002, 1696-1698.
Manzini, G. and M. Rastero (2004). "A simple and fast DNA compressor". Software—Practice and Experience 34, Feb. 2004, 1397-1411.
Behzadi, B. and F. Le Fessant (2005). "DNA compression challenge revisited." In Combinatorial Pattern Matching: Proc. of CPM-2005, LNCS, Jeju Island, Korea. Springer-Verlag.

(Continued)

*Primary Examiner* — Lori A Clow
(74) *Attorney, Agent, or Firm* — Barnes & Thornburg LLP

(57) ABSTRACT

The present subject matter discloses a system and a method for compression of genomic data. In one embodiment, the method for compression of genomic data includes obtaining modified genomic data from genomic data based at least in part on intermediary data identified from the genomic data. In one implementation, the modified genomic data includes a plurality of primary characters. The genomic data may then be modified to generate one or more most-frequent character files based at least on a most-frequent character and a second most-frequent character from among the plurality of primary characters. Further, based at least on the one or more most-frequent character files and the modified genomic data, a least-frequent characters file may be created from the modified genomic data.

18 Claims, 7 Drawing Sheets

(56) References Cited

OTHER PUBLICATIONS

Cao, M. D., T. I. Dix, L. Allison, and C. Mears (2007). "A simple statistical algorithm for biological sequence compression". In Proc. of the Data Compression Conf., DCC-2007, Snowbird, Utah.

Korodi, G. and I. Tabus (2007). "Normalized maximum likelihood model of order-1 for the compression of DNA sequences". In Proc. of the Data Compression Conf., DCC-2007, Snowbird, Utah.

Pinho, A. J., A. J. R. Neves, and P. J. S. G. Ferreira (2008). "Inverted-repeats-aware finite-context models for DNA coding". In Proc. of the 16th European Signal Processing Conf., EUSIPCO—2008, Lausanne, Switzerland.

Ristov, S. (2002). "Using inverted files to compress text. Journal of Computing and Information Technology", 10, 157-162.

"DNA Sequence Reads Compression"; http://sun.aei.polsl.pl/dsrc/index.html , 2011.

Gregory Vey, "Differential direct coding: a compression algorithm for nucleotide sequence data", The journal of biological databases and curation; Database, vol. 2009, Article ID bap013, doi:10.1093/database/bap013, 2009.

* cited by examiner

US 8,972,200 B2

COMPRESSION OF GENOMIC DATA

TECHNICAL FIELD

The present subject matter relates, in general, to the field of genomics and, in particular, to compression of genomic data.

BACKGROUND

Genome sequencing is a field of active research today. An understanding of the genome variation may enable researchers to fully understand the issues of genetic susceptibility and pharmacogenomics of drug response for all individuals as well as personalized molecular diagnostic tests. For such research or medical purposes, genetic material obtained directly from either a biological or an environmental sample is generally sequenced into a plurality of sequences, called genomic sequences. A facility, such as a research laboratory or a clinic involved in genomic study typically uses high capacity platforms, such as next generation sequencing (NGS) platforms capable of generating large number of genome sequences per year. The genomic sequence thus generated may be further processed and assembled into sets called contigs. Generally, the genomic sequences, or contigs, may be stored for future studies for further analysis. Thus, each year, genomic data, such as the genomic sequence and/or the contigs are generated in huge volumes, in the range of hundreds of terabytes (TB), and stored in the repositories.

Typically the genomic data is either archived in repositories, for example, individual repositories associated with laboratories generating the genomic data or public sequence repositories, such as Genbank, which archive data received from various laboratories in a central repository. Storage of such huge volumes of data requires the repositories to have large storage disks having huge volumes of storage capacity. Further, with the advances in the research, the genomic data may also increase, thereby increasing maintenance costs and requirements for additional storage space. Furthermore, since the genomic data may be utilized for future references, the genomic data may be archived in compressed form so as to decompress/retrieve the same without any loss of information.

SUMMARY

This summary is provided to introduce concepts related to compression of genomic data, which are further described below in the detailed description. This summary is not intended to identify essential features of the claimed subject matter nor is it intended for use in determining or limiting the scope of the claimed subject matter.

Method(s) and a system(s) for compression of genomic data are described herein. In one implementation, modified genomic data having a plurality of primary characters is obtained from genomic data based at least in part on intermediary data identified from the genomic data. The modified genomic data may then be modified to generate one or more most-frequent character files based at least on a most-frequent character and a second most-frequent character from among the plurality of primary characters. Further, a least-frequent characters file may be created from the modified genomic data based at least on the one or more most-frequent character files and the modified genomic data.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
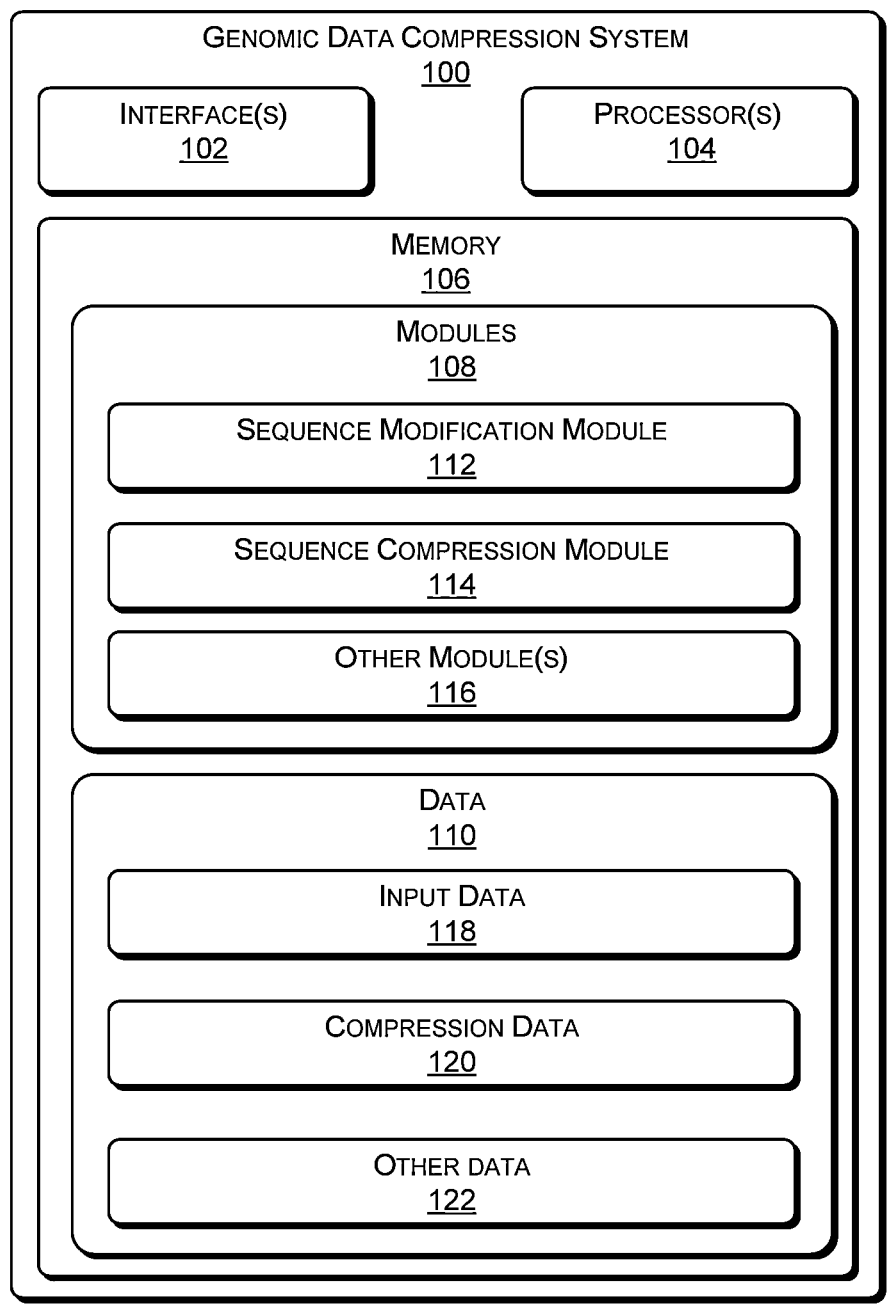
FIG. 1 illustrates a system for compression of genomic data, in accordance with an embodiment of the present subject matter.

Systems and methods for compression of genomic data are described herein. Generally, genetic material extracted directly from either a biological or an environmental sample is processed and stored as genomic data for research or medical purposes. The genomic data typically includes the genetic material sequenced into a plurality of sequences, called genomic sequences that may be further processed and assembled into sets called contigs. Generally, the genomic data may be archived in various repositories for future references.

In order to increase the efficiency of the repositories in storing the genomic data and also to reduce costs related to the storage for biological databases, the genomic data may be compressed before being stored. Conventional compression techniques employed by sequence repositories or databases are based on compression techniques that are generally used for compression of text files and are thus unable to optimally compress the genomic data. Some specialized genomic data compression algorithms exist, whose working principle is based on identification of repeated patterns of known bases prevalent within the genomic sequences. However, in addition to known bases or primary characters, some intermediary data, for example, secondary characters or use of symbols to represent gaps of indeterminate length may also be present in the genomic sequences. Most of the reported implementations of data compression algorithms specialized for the compression of genomic data, may not identify or handle such characters. An inaccurate compression/decompression of the genomic sequence may in turn lead to loss of the genomic information.

Additionally, certain other algorithmic implementations specialized for genomic data compression, may have high compression and/or decompression time and memory requirements, thus increasing the processing costs. An inefficient compression/decompression of the genomic data in terms of time taken may additionally affect research by hindering quick and efficient storage, retrieval, and transmission of the genomic data.

The present subject matter describes methods and systems for compression of genomic data. The genomic data includes a plurality of genomic sequences. The genomic sequences include, for example, and not as a limitation, nucleotide sequences, Deoxyribonucleic acid (DNA) sequences, ribonucleic acid (RNA), and amino acid sequences. Although the description herein is in considerable detail with respect to a nucleotide sequence, it will be understood that the methods and systems for compression can be implemented for other genomic sequences as well, albeit with a few variations, as will be understood by a person skilled in the art.

According to an embodiment of the present subject matter, genomic data having a plurality of genomic sequences is received for compression. A genomic sequence, as will be known to a person skilled in the art, typically includes data in the form of primary characters, and is preceded by a header section having information, hereinafter referred to as header information, about the genomic sequence. For instance, data in nucleotide sequences may be represented in the form of primary characters 'A', 'T', 'G', and 'C', which correspond to four nucleotide bases, adenine (A), thymine (T), guanine (G), and cytosine (C), while the header information includes data, such as an ID of the project for which the nucleotide sequence is generated and sequence ordering.

Further, genomic sequences may also include secondary characters, such as non-ATGC characters, like 'Y', 'W', 'M', 'K', 'B', 'V', 'D', 'N', 'H', 'R', and 'S' in the case of nucleotide sequences. Further, certain other characters may also represent repetitive stretches of a particular nucleotide base and regions of low complexity using lower case characters. For instance, in a nucleotide sequence having four standard nucleotide bases, ATGC, a long stretch of a character, say, 'G' may be represented using the lower case character 'g'. For the ease of understanding, and not as a limitation, all the secondary characters and other information other than the character of interest, i.e., the primary characters in the genomic data may be collectively referred to as intermediary data. For instance, in case of DNA sequences, A, T, G, and C may be the primary characters and in case of an RNA sequence, A, U, G, and C may be the primary characters. Additionally, the primary characters may also be determined based on a user input. For example, in a particular scenario a secondary character, say 'S' may be included in primary characters.

In order to have a loss-less and efficient compression, the genomic data is initially classified into the intermediary data and the primary characters. The intermediary data thus identified is subsequently used to modify the genomic data to receive modified genomic data. For example, the header files corresponding to all the genomic sequences present in the genomic data may be removed and stored as header files and all the lower case characters may be converted to upper case characters. Further, the secondary characters, such as 'H', 'N' or '-' may be removed. The modified genomic data thus includes only a plurality of the primary characters. For instance, the modified genomic data for nucleotide sequences may only include a plurality of primary characters A', 'T', 'G', and 'C.

The modified genomic data is then analyzed to compute frequency of occurrence of each of the primary characters present in the modified genomic data. Based on the computation, the primary characters may be listed in an increasing or decreasing order of their respective frequencies to identify a most-frequent character, a second most-frequent character, and one or more least-frequent characters. The most-frequent character and the second most-frequent character are subsequently used to generate one or more most-frequent character files.

In one embodiment, absolute positions of the most-frequent character in the modified genomic data are identified and a delta difference between the successive positions of the most-frequent character is computed to generate a first character file. The most-frequent character may then be removed from the modified genomic data to obtain an intermediate file. The intermediate file is then analyzed to identify absolute positions of a current most-frequent character in the intermediate file, i.e., the second most-frequent character in the modified genomic data. Again, a delta difference between the successive positions of the second most-frequent character is computed to generate a second character file. The first character file and the second character file are subsequently identified as the most-frequent character files. Further, the second most-frequent character is then removed from the intermediate file to generate a least-frequent characters file having only the least-frequent characters.

In another embodiment, absolute positions of the most-frequent character and the second most-frequent character in the modified genomic data are identified and a delta difference between the successive positions of the most-frequent character and the second most-frequent character is computed to generate a positions file. Further, order of occurrence of the second most-frequent character and the most-frequent character may be identified and stored in an occurrence file. The positions file and the occurrence file are subsequently identified as the most-frequent character files. Further, the most-frequent character and the second most-frequent character are removed from the modified genomic data to generate the least-frequent characters file.

The least-frequent characters file, the most-frequent character files, and the intermediary data are then compressed together to generate a final output file, referred to as compressed genomic data that can be archived for further processing and/or future references. Due to the compression of data at various stages, the compressed genomic data thus obtained is not only efficient in terms of compression ratio and compression time but is also lossless in terms of accuracy. The provision for, identification and separation of the intermediary data from the primary characters ensures reduction of redundant bit allocation for the intermediary data, such as lower case characters and the secondary characters. In addition, saving the two most-frequent characters and the two least-frequent characters separately ensures that lesser data bits are required for storing the data. For instance, delta encoding of the positions of the most-frequent and the second most-frequent characters provides lower delta values, which when unary coded take lesser number of bits than would have been required for unary encoded delta values for the least-frequent characters. Further, saving the two least-frequent characters in a binary encoded form facilitates using lesser bits.

Although the description herein is with reference to certain sequences, the systems and methods may be implemented for other sequences as well, albeit with a few variations, as will be understood by a person skilled in the art.

While aspects of described systems and methods for compression of genomic sequences can be implemented in any number of different computing systems, environments, and/or configurations, the embodiments are described in the context of the following exemplary system(s).

FIG. 1 illustrates a genomic data compression system 100, according to an implementation of the present subject matter.

The genomic data compression system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the genomic data compression system 100, hereinafter referred to as, the system 100 includes interface(s) 102, one or more processor(s) 104, and a memory 106 coupled to the processor(s) 104.

The interfaces 102 may include a variety of software and hardware interfaces, for example, interfaces for peripheral device(s), such as a keyboard, a mouse, an external memory, and a printer. Further, the interfaces 102 may enable the system 100 to communicate with other devices, such as web servers and external databases. The interfaces 102 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 102 may include one or more ports for connecting a number of computing systems with one another or to another server computer.

The processor(s) 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 also includes module(s) 108 and data 110.

The modules 108, amongst other things, include routines, programs, objects, components, data structures, etc., which perform particular tasks or implement particular abstract data types. The modules 108 further include a sequence modification module 112, a sequence compression module 114, and other module(s) 116. The other modules 116 may include programs that supplement applications on the system 100, for example, programs in the operating system. On the other hand, the data 110 serves, amongst other things, as a repository for storing data processed, received, and generated by one or more of the modules 108. The data 110 includes input data 118, compression data 120, and other data 122. The other data 122 includes data generated as a result of the execution of one or more modules in the other modules 116.

In one implementation, the system 100 is associated with a sequence database (not shown in the figure). The sequence database includes a plurality of genomic sequences generated by a genomic data generation platform, such as an NGS based platform. The genomic sequences, as will be understood, are in a raw and uncompressed form and are provided to the system 100 for compression. Although the description system and the methods herein is in considerable detail with respect to a nucleotide sequence, it will be understood that the methods and systems for compression can be implemented for other genomic sequences, such as DNA sequences, RNA sequences, and amino acid sequences as well, albeit with a few variations, as will be understood by a person skilled in the art.

The system 100, in one implementation, receives genomic data having a plurality of genomic sequences from the sequence database. For the purpose of explanation, and not as a limitation, the foregoing description is made with reference to the following example. It will be understood that the principles described herein can be extended to other scenarios as well.

For example, the system 100 may receive the following nucleotide sequences as the genomic data having three genomic sequences (identified below as SEQ. ID NO.1, SEQ. ID NO.2, and SEQ. ID NO.3 in >SAM_READ_00151942, >SAM_READ_00152628, and >SAM_READ_00153187, respectively).

```
>SAM_READ_00151942/accession = SAM_READ_00151942/name = 862.x6/ti = 2229088753/
library_id = BIZP/template_id = BIZP 11862/mate_ti = 2229088754/sequencing_direction = FOR-
WARD/
NCBI_project_ID = 37811/clr_range_begin=/clr_range_end=/full_length = 1203/number_of_sites =
1/
length = 1203/sample_id = 1380619975823197451/sample_acc = SAM_SMPL_SAMPLE2
sample_name = SAM_SMPL_SAMPLE2/site_id_n = SAM_SITE_SAMPLE2
TGGGGNNNNNNNNNNNNNNNNANACGGGGTTGCGGNTACGACGGCAGNGCANTGTATACGACTCACTA

TAGGGCGAATTGGGCCTCTAGATGCATGCTCGAGCGGCCGCCAGTGTGATGGATATCTGCAGAATTCG

CCCTTGGGGTTCATACACCAGCCGGGCGACGATCTGGCCGTGTTCCAGCAGGAAGGGGGTGTCGTG

GGTGCGGACCTCCAGCACGCCCTTGGAGCCCGCGCCATGCGCTTCGTCCGTGCCGAAGCCGGGGTC

GAAGAAGCCGGCGTAGTGGACGCGGAACTCGCCCACAGACGGGTCGATGGGGGTCATTTCGGCGGC

CTGATCGACCGGGATCTCCACGTCGTCGGACGAGGCCAGGATGTAGAACTCGCCCGGATCCAAGAGC

AGCTCGCCACGACGTAGGCTCAGCGGCTCCCAGAAGTCGCGCGGATCGTGGCCGTCGATATGGTCCA

GATCGACCACCCCGGCATGGCGGCGGCCGCGGAAGCCGCCCCAAACAATACAGCCGAAAGCTAAGT

GTAAGCGCGGGGTGAG

>SAM_READ_00152628/accession = SAM_READ_00152628/name = 838.b2/ti = 2229097151/
library_id = BIZP/template_id = BIZP 16838/mate_ti = 2229097152/sequencing_direction = FOR-
WARD/
NCBI_project_ID = 37811/clr_range_begin=/clr_range_end=/full_length = 923/number_of_sites =
1/
length = 923/sample_id = 1380619975823197451/sample_acc = SAM_SMPL_SAMPLE2
sample_name = SAM_SMPL_SAMPLE2/site_id_n = SAM_SITE_SAMPLE2
```

-continued

```
CCCCTTCAGCAGGATGTATAGACTCCTATAGGGCGAATTGGGCCCTCTAGATGCATGCTCGAGCGGCC

GCCAGTGTGATGGATATCTGCAGAATTCGCCCTTCCTCGCTATCCATTTGGTCATGGTCTCAGCTACAC

AACGTTCAAGTACTCAGATCTCAAGATCAAATCTCAGGGTATCGAGGCCGGACCAGCGACTGGGCACG

CGTTTGGTGGGACGCCGTTTGATATCGGAGCGGGCATTGTGGTGGCTGCAATGTATTAGATTATGACA

AGATGCTCTTCCTGGCCAGAGAAACGCAGCAAGCTCGTTGTCATCAGAGAACCAAAGCTTTGATATCTA

CGTCTTTATACTCTCCAATCTCGGCGCAGCGGACATCAAGCGCCTTTCGACCATTAACAGTGGGAAGAT

ACCCAAGGTACCCCTCTCTTCTTCACATCCTGTGGTTTGTGTATGGCTGTCGCTTGACGGCGCAGCTC

GAACCCTGCATGCCACGCATGCGGAGTATTGCCTGCGTCATGGTGTCACAAAGGGCGAATTTCAGCAC

ACTGGCGGTCGTTACTAGGGAATCCGAGCTTCGTACCAGGCTGATGCATAGCTTGAGTATTCTATAGTG

T

>SAM_READ_00153187/accession = SAM_READ_00153187/name = 448.y3/ti = 2229085927/
library_id = BIZP/template_id = BIZP10448/mate_ti = 2229085926/sequencing_direction =
REVERSE/
NCBI_project_ID = 37811/clr_range_begin=/clr_range_end=/full_length = 1177/number_of_sites =
1/
length = 1177/sample_id = 1380619975823197451/sample_acc = SAM_SMPL_SAMPLE2/
sample_name = SAM_SMPL_SAMPLE2/site_id_n = SAM _SITE_SAMPLE2
GAAAGCAATAAAGaaaaaaaaaaaaaaaaaaaaaaaaaaaaaaaaaaaaaaaaaaaaaaaaaaaaaaaaaATGCCCANN

NNNNNNNNNNNCNGAGAGCGGCGCCAAGCATAGGTGAATATAGAATTCAGCTATGCATCAGCTTGGTA

CCGAGCTCGGATCCACTAGTAACGGCCGCCAGTGTGCTGGAATTCGCCCTTGACGCAGGCCGCCAAC

TACGCCAAGTCGGGTCGTCCGACGCGCGNTCTGATCGTCGGCTACACCGACACCTCGGGTTCGGCCG

CCTATAACCTGGGTCTGTCCAACCGTCGTTCGCGCACCGTCGCGGACGCCCTGGTGGCTCAAGGCGT

CAACGGCGGCGTGATCGCCCTGGACGGCAAGGGCGAAACCAACCTGGCCAAGCCCACCGCCGACGG

CGTGCGTGAACCGCTCAACCGCCGCGCGACCATCGACATCAACTTCTAAGACCCAATGGAAAGCCGG

TCTGGACAACCAGACCGGCGATCCTGAGGATCAGATGTCGAACGACTTTTGACGCCGTCTCCGAAAGG

GGGCGGCGTTTCTGTTTGCGTAGAAGGGTCAGTCTTGAGCGGTGACGGTCAACGGCGGGCTTGGCGC

GCTGAACGATTGTCGGCTTAGAACCGCCTCGCCAAGCGCGATCACCACGGTCGCCGTCAGAAGGGCG

CAGACCACCGCGACGGCGGCCAGCTTCAGGCCTTGTCCAAAATCCCAGTCGTCCGGCGTCACGGCGT

CGCTCCTGCGGAGGGCTTTGCTCGGCCTAACCCCGATGTTCGACATCCCGCAAGCGCGACCGGCGG

GCAGGGATGCGAAAAGGGCGACGTCTTGCGACGCCGCCCCGATGATCTTTCCCTGATGTCGATC
```

The genomic data to be compressed may be saved in the input data 118. Each of the genomic sequences in the genomic data includes data in the form of primary characters. For instance, data in nucleotide sequences is represented in the form of characters 'A', 'T', 'G', and 'C', known as nucleotide bases. Additionally, each of the genomic sequence is preceded by a header section having information, hereinafter referred to as header information, about the genomic sequence, thus marking a beginning of the genomic sequence. For example, the header information includes data, such as an ID of the project for which the sequence is generated and sequence ordering. In the above example of the genomic data, the header information begins with ">SAM_READ" and ends with "SAMPLE2".

Further, the genomic sequences generated may include secondary characters in addition to the primary characters. For instance, in a nucleotide sequence, non-ATGC characters, such as 'N', 'H', 'R', and 'S' may also be present. Referring to the example discussed above, character 'N' is also present apart from the ATGC characters in the first and third genomic sequences. The character 'N' may be taken as a secondary character. Furthermore, such generators may also represent repetitive stretches of a particular nucleotide base and regions of low complexity using lower case characters. For instance, in a nucleotide sequence a long stretch of a character, say, 'G' may be represented using the lower case character 'g'. In the above example of the genomic data, lower case character 'a' is present in order to indicate a long stretch of the character 'A'. For the ease of understanding, and not as a limitation, all the information, except the bases, in the genomic data, may be collectively referred to as intermediary data.

In one implementation, the intermediary data is identified and removed from the genomic data to facilitate efficient compression. For the purpose, the sequence modification module 112 accesses the input data 118 to obtain the genomic data. The sequence modification module 112 initially analyzes the genomic data to identify the header files associated with each of the genomic sequences. The sequence modification module 112 may identify the header files based on one or more preconfigured parameters or rules. For instance, the sequence modification module 112 may be configured to identify all the information between the symbol '>' and information pertaining to site_id as the header information. Subsequently, the sequence modification module 112 may determine the length of each of the genomic sequences and append it to the respective header information. In one implementation, the sequence modification module 112 appends the length of each of the genomic sequences in the beginning of the associated header information. In another implementation, the sequence modification module 112 appends the length of each of the genomic sequences at the end of the associated header information.

Based on the header information of each of the genomic sequences along with length of the associated genomic sequence the sequence modification module 112 generates a header file. For instance, in the previous example of the genomic data received by the system 100, the sequence modification module 112 may analyze the genomic data to generate the header file as follows:

```
549>SAM_READ_00151942   /accession=SAM_READ_00151942   /name=862.x6   /ti=2229088753
/library_id=BIZP   /template_id=BIZP11862   /mate_ti=2229088754   /sequencing_direction=FORWARD
/NCBI_project_ID=37811   /clr_range_begin=   /clr_range_end=   /full_length=1203   /number_of_sites=1
/length=1203      /sample_id=1380619975823197451      /sample_acc=SAM_SMPL_SAMPLE2
/sample_name=SAM_SMPL_SAMPLE2 /site_id_n=SAM_SITE_SAMPLE2
617>SAM_READ_00152628   /accession=SAM_READ_00152628   /name=838.b2   /ti=2229097151
/library_id=BIZP   /template_id=BIZP16838   /mate_ti=2229097152   /sequencing_direction=FORWARD
/NCBI_project_ID=37811   /clr_range_begin=   /clr_range_end=   /full_length=923   /number_of_sites=1
/length=923      /sample_id=1380619975823197451      /sample_acc=SAM_SMPL_SAMPLE2
/sample_name=SAM_SMPL_SAMPLE2 /site_id_n=SAM_SITE_SAMPLE2
876>SAM_READ_00153187   /accession=SAM_READ_00153187   /name=448.y3   /ti=2229085927
/library_id=BIZP   /template_id=BIZP10448   /mate_ti=2229085926   /sequencing_direction=REVERSE
/NCBI_project_ID=37811   /clr_range_begin=   /clr_range_end=   /full_length=1177   /number_of_sites=1
/length=1177     /sample_id=1380619975823197451      /sample_acc=SAM_SMPL_SAMPLE2
/sample_name=SAM_SMPL_SAMPLE2 /site_id_n=SAM_SITE_SAMPLE
```

For the sake of clarity, the header information corresponding to each of the genomic sequences has been indicated as separate entries, it will be understood that the header information of all the genomic sequences may be combined together as a single sentence or an entry. The sequence modification module 112 may subsequently save the header file in the compression data 120.

Further, the sequence modification module 112 may determine one or more regions of low complexity in the genomic data. In one implementation, the sequence modification module 112 may identify all stretches of lower case characters present in the genomic data. On identification of the stretches of the lower case characters, the sequence modification module 112 determines start and end positions of the stretches. Further, the sequence modification module 112 calculates a first delta difference between positions of two consecutive stretches to calculate length of a stretch. In one implementation, the first delta difference for a stretch may be calculated by subtracting the value of the start position from the end position of the stretch. Further, a second delta difference between consecutive stretches may be calculated by subtracting the end position of a preceding stretch from the start position of a following stretch. The sequence modification module 112 subsequently generates a lower case character file having the first delta difference for each of the stretches and the second delta difference between consecutive stretches. In one implementation, the delta difference may be stored in the lower case character using the following pattern:

```
StartPosition1,(EndPosition1-StartPosition1),
(StartPosition2-EndPosition1), (EndPosition2-StartPosition2),
(StartPosition3-EndPosition2),   (EndPosition3-StartPosition3).....
(StartPosition[N]-EndPosition[N-1]),
(EndPosition[N]-StartPositionN)
```

Referring to the example discussed above, the sequence modification module 112 may analyze the genomic data and may identify a stretch of lower case character 'a' beginning at the position 1180 and ending at the position 1238. The sequence modification module 112 may generate the lower case character file as follows:

The lower case character file, thus generated, may be saved in the compression data 120.

The sequence modification module 112 subsequently determines absolute positions of all the secondary characters present in the genomic data being compressed. The absolute position of a character may be understood as the position of the character in the genomic data with reference to the first character. For example, if in the genomic data the first genomic sequence starts with 'A' followed by 'N' then the absolute position of 'N' would be 2. Similarly, if the first sequence, is of, say, 500 characters, and the second genomic sequence begins with 'N' then absolute positions of 'N' will, at least, be 2 and 501. Based on the determination, the sequence modification module 112 computes delta difference between the absolute positions of adjacent secondary characters. A secondary characters file may then be generated and saved in the compression data 120 by the sequence modification module 112 based on the delta difference between the absolute positions of adjacent secondary characters. In one implementation, the delta difference may be stored in the secondary characters file using the following pattern:

```
Position1,Character,(Position2-Position1),
Character,(Postion3-Position2), Character, ........,
(Position[N]- Position[N-1]),Character
```

For instance, in the previous example of the genomic data, since the only additional secondary character in the genomic data is 'N', the sequence modification module 112 may analyze the genomic data to determine the absolute positions of the secondary character 'N' as follows:

6 7 8 9 10 11 12 13 14 15 16 17 18 19 20 22 35 47 51 1240 1241 1242 1243 1244 1245 1246 1247 1248 1249 1250 1251 1252 1254 1406

The sequence modification module 112 then generates a secondary characters file as follows:

6N1N1N1N1N1N1N1N1N1N1N1N1N1N1N2N13N12N 4N1189N1N1N1N1N1N1N1N1N1N1N1N2N152N

The secondary characters file, the header file, and the lower case characters file are subsequently used to modify the genomic data to obtain modified genomic data. In one implementation, the sequence modification module 112 removes all the secondary characters and the headers from the genomic data. Further, the lower case characters, may be replaced by corresponding upper case characters. The modified genomic data thus obtained includes only the characters representing the primary characters. For instance, in the previous example of the genomic data, the sequence modification module 112 removes all the secondary characters and the headers from the genomic data to create the modified genomic data as follows (SEQ. ID NO.4):

```
TGGGGAACGGGGTTGCGGTACGACGGCAGGCATGTATACGACTCACTATAGGGCGAATTGGGCCTCT

AGATGCATGCTCGAGCGGCCGCCAGTGTGATGGATATCTGCAGAATTCGCCCTTGGGGTTCATACACC

AGCCGGGCGACGATCTGGCCGTGTTCCAGCAGGAAGGGGGTGTCGTGGGTGCGGACCTCCAGCACG

CCCTTGGAGCCCGCGCCATGCGCTTCGTCCGTGCCGAAGCCGGGGTCGAAGAAGCCGGCGTAGTGG

ACGCGGAACTCGCCCACAGACGGGTCGATGGGGGTCATTTCGGCGGCCTGATCGACCGGGATCTCCA

CGTCGTCGGACGAGGCCAGGATGTAGAACTCGCCCGGATCCAAGAGCAGCTCGCCACGACGTAGGCT

CAGCGGCTCCCAGAAGTCGCGCGGATCGTGGCCGTCGATATGGTCCAGATCGACCACCCCGGCATG

GCGGCGGCCGCGGAAGCCGCCCCAAACAATACAGCCGAAAGCTAAGTGTAAGCGCGGGGTGAGCCC

CTTCAGCAGGATGTATAGACTCCTATAGGGCGAATTGGGCCCTCTAGATGCATGCTCGAGCGGCCGCC

AGTGTGATGGATATCTGCAGAATTCGCCCTTCCTCGCTATCCATTTGGTCATGGTCTCAGCTACACAAC

GTTCAAGTACTCAGATCTCAAGATCAAATCTCAGGGTATCGAGGCCGGACCAGCGACTGGGCACGCGT

TTGGTGGGACGCCGTTTGATATCGGAGCGGGCATTGTGGTGGCTGCAATGTATTAGATTATGAGAAGA

TGCTCTTCCTGGCCAGAGAAACGCAGCAAGCTCGTTGTCATCAGAGAACCAAAGCTTTGATATCTACGT

CTTTATACTCTCCAATCTCGGCGCAGCGGACATCAAGCGCCTTTCGACCATTAACAGTGGGAAGATACC

CAAGGTACCCCTCTCTTCTTCACATCCTGTGGTTTGTGTATGGCTGTCGCTTGACGGCGCAGCTCGAAC

CCTGCATGCCACGCATGCGGAGTATTGCCTGCGTCATGGTGTCACAAAGGGCGAATTTCAGCACACTG

GCGGTCGTTACTAGGGAATCCGAGCTTCGTACCAGGCTGATGCATAGCTTGAGTATTCTATAGTGTGAA

AGCAATAAAGAAAAAAAAAAAAAAAAAAAAAAAAAAAAAAAAAAAAAAAAAAAAAAAAAAAAAAAAAC

GAGAGCGGCGCCAAGCATAGGTGAATATAGAATATCAGCTATGCATCAGCTTGGTACCGAGCTCGGAT

CCACTAGTAACGGCCGCCAGTGTGCTGGAATTCGCCCTTGACGCAGGCCGCCAACTACGCCAAGTCG

GGTCGTCCGACGCGCGTCTGATCGTCGGCTACACCGACACCTCGGGTTCGGCCGCCTATAACCTGGG

TCTGTCCAACCGTCGTTCGCGCACCGTCGCGGACGCCCTGGTGGCTCAAGGCGTCAACGGCGGCGT

GATCGCCCTGGACGGCAAGGGCGAAACCAACCTGGCCAAGCCCACCGCCGACGGCGTGCGTGAACC

GCTCAACCGCCGCGCGACCATCGACATCAACTTCTAAGACCCAATGGAAAGCCGGTCTGGACAACCAG

ACCGGCGATCCTGAGGATCAGATGTCGAACGACTTTGACGCCGTCTCCGAAAGGGGCGGCGTTTCT

GTTTGCGTAGAAGGGTCAGTCTTGAGCGGTGACGGTCAACGGCGGGCTTGGCGCGCTGAACGATTGT

CGGCTTAGAACCGCCTCGCCAAGCGCGATCACCACGGTCGCCGTCAGAAGGGCGCAGACCACCGCG

ACGGCGGCCAGCTTCAGGCCTTGTCCAAAATCCCAGTCGTCCGGCGTCACGGCGTCGCTCCTGCGGA

GGGCTTTGCTCGGCCTAACCCCGATGTTCGACATCCCGCAAGCGCGACCGGCGGGCAGGGATGCGA

AAAGGGCGACGTCTTGCGACGCCGCCCCGATGATCTTTCCCTGATGTCGATC
```

The modified genomic data may be stored in the compression data 120. The modified genomic data may then be processed by the sequence compression module 114 to obtain compressed genomic data. The sequence compression module 114 may analyze the modified genomic data to compute a frequency of occurrence of each of the primary characters present in the modified genomic data. Based on the computation, the sequence compression module 114 may identify a most-frequent character, a second most-frequent character, and one or more least-frequent characters. The sequence compression module 114 may obtain the compressed genomic data based on the most-frequent character, the second most-frequent character, and the least-frequent characters. For instance, in the above example of the genomic data received by the system 100, the sequence compression module 114 may analyze the modified genomic data to identify the frequency of the primary characters 'A', 'G', 'T', and 'C' as 463, 594, 378, and 573, respectively. Based on the identification, the sequence compression module 114 may identify 'G' as the most-frequent character, 'C' as the second most-frequent character, and 'A' and 'T' as the least-frequent characters.

In one embodiment of the genomic data compression, the sequence compression module 114 analyzes the modified genomic data to identify absolute positions of the most-frequent character. Based on the absolute positions, the sequence compression module 114 may compute a delta difference between successive positions of the most-frequent character. A first character file having the delta difference may be generated by the sequence compression module 114.

Referring to the example discussed above, the sequence compression module 114 may analyze the modified genomic data to identify the absolute positions of the most-frequent character 'G' as follows:

frequent character in the intermediate file, i.e., the second most-frequent character in the modified genomic data. Based on the absolute positions, the sequence compression module 114 computes a delta difference between the successive posi- 2 3 4 5 9 10 11 12 15 17 18 22 25 26 29 30 34 40 51 52 53 55 60 61 62 69 72 76 80 82 84 85 88 92 94 96 99
100 107 110 116 122 123 124 125 137 140 141 142 144 147 152 153 156 158 164 167 168 171 172 173 174
175 177 180 182 183 184 186 188 189 197 201 207 208 210 214 216 221 223 228 232 234 237 240 243 244
245 246 249 252 255 258 259 261 264 266 267 270 272 273 279 286 289 290 291 294 297 298 299 300 301
309 310 312 313 317 321 325 326 327 336 339 342 343 346 348 349 353 354 357 360 366 370 371 378 380
383 387 392 395 398 399 404 406 407 414 417 420 422 424 425 429 431 432 435 438 443 444 449 453 462
463 467 468 470 471 473 474 477 479 480 483 486 501 504 508 513 515 519 521 523 524 525 526 528 530
539 542 543 546 551 561 562 563 565 570 571 572 580 583 587 591 593 595 596 599 603 605 607 610 611
618 621 627 637 648 649 654 655 661 671 677 684 692 704 705 706 711 713 714 717 718 723 725 729 730
731 735 737 741 742 744 745 746 749 752 756 762 763 765 767 768 769 774 776 777 779 780 783 788 794
800 805 808 817 818 822 824 829 832 836 840 843 850 852 860 865 874 895 896 898 901 903 904 912 914
921 932 934 935 936 939 948 949 973 975 976 980 982 986 987 990 993 997 1000 1001 1003 1006 1010
1017 1021 1026 1030 1032 1033 1035 1040 1044 1046 1051 1052 1054 1062 1063 1064 1066 1074 1081
1082 1084 1085 1088 1095 1096 1097 1103 1105 1110 1116 1117 1120 1123 1128 1132 1134 1144 1146
1148 1152 1160 1222 1224 1226 1228 1229 1231 1236 1241 1242 1244 1251 1259 1264 1270 1274 1275
1280 1282 1286 1287 1296 1301 1302 1305 1309 1311 1313 1316 1317 1323 1329 1332 1335 1336 1339
1348 1353 1356 1357 1358 1361 1365 1368 1370 1372 1376 1380 1383 1384 1392 1400 1401 1402 1406
1407 1410 1421 1422 1423 1427 1435 1438 1442 1444 1449 1452 1454 1455 1458 1463 1464 1466 1467
1473 1474 1476 1482 1483 1485 1486 1488 1490 1494 1499 1500 1503 1504 1508 1509 1510 1512 1523
1524 1529 1536 1539 1542 1543 1545 1547 1549 1551 1556 1564 1567 1569 1571 1578 1593 1601 1602
1606 1609 1610 1614 1615 1623 1627 1628 1630 1636 1638 1639 1644 1647 1650 1654 1660 1663 1666
1672 1676 1677 1678 1679 1680 1682 1683 1685 1691 1695 1697 1700 1703 1704 1705 1709 1714 1716
1718 1719 1721 1724 1725 1731 1732 1734 1735 1736 1740 1741 1743 1745 1748 1752 1756 1759 1760
1765 1770 1775 1780 1782 1784 1793 1794 1797 1800 1804 1807 1808 1809 1811 1814 1821 1823 1826
1827 1829 1830 1834 1840 1841 1846 1859 1862 1866 1867 1869 1874 1875 1877 1880 1886 1888 1889
1891 1892 1893 1898 1902 1903 1913 1916 1920 1928 1932 1934 1936 1940 1941 1943 1944 1945 1948
1949 1950 1953 1955 1960 1961 1962 1964 1967 1972 1974 1977 1980 1985 1988 1999 2002 2005

The first character file having the delta difference may then be generated by the sequence compression module 114 as follows:

tions of the current most-frequent character in the intermediate file to generate a second character file.

2 1 1 1 1 4 1 1 1 3 2 1 4 3 1 3 1 4 6 1 1 1 2 5 1 1 7 3 4 4 2 2 1 3 4 2 2 3 1 7 3 6 6 1 1 1 1 2 3 1 1 2 3 5 1 3 2 6
3 1 3 1 1 1 1 2 3 2 1 1 2 2 1 8 4 6 1 2 4 2 5 2 5 4 2 3 3 3 1 1 1 3 3 3 3 1 2 3 1 3 2 1 6 7 3 1 1 3 3 1 1 1 8 1 2 1
4 4 4 1 1 9 3 3 1 3 2 1 4 1 3 3 6 4 1 7 2 3 4 5 3 3 1 5 2 1 7 3 3 2 2 1 4 2 1 3 3 5 1 5 4 9 1 4 1 2 1 2 1 3 2 1 3 3
1 5 3 4 5 2 4 2 2 1 1 1 2 2 9 3 1 3 5 1 0 1 1 2 5 1 1 8 3 4 4 2 2 1 3 4 2 2 3 1 7 3 6 1 0 1 1 1 5 1 6 1 0 6 7 8 1 2 1 1 5
2 1 3 1 5 2 4 1 1 4 2 4 1 2 1 1 3 3 4 6 1 2 2 1 1 5 2 1 2 1 3 5 6 6 5 3 9 1 4 2 5 3 4 4 3 7 2 8 5 9 2 1 1 2 3 2 1 8 2
7 1 1 2 1 1 3 9 1 2 4 2 1 4 2 4 1 3 3 4 3 1 2 3 4 7 4 5 4 2 1 2 5 4 2 5 1 2 8 1 1 2 8 7 1 2 1 3 7 1 1 6 2 5 6 1 3 3 5
4 2 1 0 2 2 4 8 6 2 2 2 2 1 2 5 5 1 2 7 8 5 6 4 1 5 2 4 1 9 5 1 3 4 2 2 3 1 6 6 3 3 1 3 9 5 3 1 1 3 4 3 2 2 4 4 3 1 8
8 1 1 4 1 3 1 1 1 1 4 8 3 4 2 5 3 2 1 3 5 1 2 1 6 1 2 6 1 2 1 2 4 5 1 3 1 4 1 1 2 1 1 1 5 7 3 3 1 2 2 2 2 5 8 3 2 2 7
1 5 8 1 4 3 1 4 1 8 4 1 2 6 2 1 5 3 3 4 6 3 3 6 4 1 1 1 1 2 1 2 6 4 2 3 3 1 1 4 5 2 2 1 2 3 1 6 1 2 1 1 4 1 2 2 3 4 4
3 1 5 5 5 5 2 2 9 1 3 3 4 3 1 1 2 3 7 2 3 1 2 1 4 6 1 5 1 3 3 4 1 2 5 1 2 3 6 2 1 2 1 1 5 4 1 1 0 3 4 8 4 2 2 4 1 2 1
1 3 1 1 3 2 5 1 1 2 3 5 2 3 3 5 3 1 1 3 3

The sequence compression module 114 then removes the most-frequent characters from the modified genomic data to obtain an intermediate file having only second most-frequent character and the least-frequent characters. The sequence compression module 114 subsequently analyzes the intermediate file to identify absolute positions of a current most- Again referring to the example discussed above, the sequence compression module 114 may analyze the intermediate file to identify the absolute positions of the current most-frequent character, i.e., the second most-frequent character in the modified genomic data 'C' as follows:

4 7 10 12 13 15 22 24 26 28 33 38 39 41 46 49 51 53 54 55 56 57 67 69 75 76 77 78 83 87 89 90 92 93 94 96
99 101 102 106 107 109 115 118 120 121 123 124 126 128 129 130 131 135 136 137 138 139 140 143 144
147 149 150 152 153 156 157 159 164 165 166 171 172 175 177 178 179 180 182 185 187 191 196 197 198
199 203 205 206 209 211 212 214 216 218 220 222 223 231 233 234 235 236 239 240 244 246 248 249 250
252 254 257 259 261 262 264 265 266 271 272 273 276 278 279 281 287 288 292 294 295 297 298 299 300
301 304 305 306 307 308 311 312 313 314 315 316 320 325 327 328 332 340 341 344 345 346 347 350 352
361 363 364 369 374 375 376 378 383 386 388 390 391 392 393 394 404 406 412 413 414 415 418 419 421
422 426 427 433 437 439 441 444 446 449 452 457 459 463 465 470 475 477 482 484 485 487 488 490 492
494 496 497 503 504 505 513 515 516 522 524 539 544 546 549 550 552 553 559 560 562 565 567 571 574
579 580 584 592 595 597 604 606 608 609 613 615 616 617 619 621 624 627 628 629 633 635 636 642 650
651 652 657 658 659 660 662 664 667 670 672 675 676 686 689 690 694 695 696 698 700 703 704 705 707
710 711 713 714 717 723 724 726 728 733 735 739 745 747 749 751 753 755 759 765 766 768 771 774 775
777 781 785 793 803 870 873 874 875 876 879 895 897 901 904 906 911 912 914 916 919 920 922 928 929
930 931 932 936 942 943 944 945 949 950 952 953 954 955 958 961 962 963 967 969 971 972 974 975 976
978 982 984 985 988 990 991 993 995 996 998 1001 1002 1003 1004 1005 1011 1012 1015 1018 1019 1022
1023 1025 1028 1029 1030 1032 1033 1035 1036 1038 1039 1040 1041 1044 1046 1049 1051 1054 1055

-continued

```
1056 1060 1061 1062 1063 1066 1067 1070 1074 1075 1078 1079 1081 1082 1085 1086 1087 1089 1090
1091 1092 1094 1095 1097 1101 1102 1103 1105 1108 1109 1110 1111 1112 1113 1115 1116 1119 1121
1124 1127 1130 1135 1136 1137 1144 1145 1147 1150 1153 1154 1157 1158 1159 1162 1163 1168 1173
1176 1178 1183 1184 1185 1187 1189 1190 1194 1195 1199 1204 1210 1213 1217 1220 1222 1225 1226
1227 1230 1231 1232 1236 1241 1242 1248 1249 1250 1251 1253 1254 1255 1258 1259 1262 1264 1265
1267 1269 1270 1271 1273 1277 1278 1281 1282 1284 1285 1286 1288 1289 1290 1291 1293 1296 1298
1299 1303 1304 1310 1311 1312 1315 1317 1318 1319 1321 1323 1324 1326 1327 1329 1330 1332 1334
1338 1340 1341 1342 1346 1347 1348 1349 1354 1356 1359 1360 1361 1362 1365 1366 1368 1369 1370
1371 1375 1380 1382 1384 1387 1389 1390 1391 1392 1393 1394 1395 1400 1404 1405 1406 1411 1414
```

The second character file having the delta difference may then be generated by the sequence compression module 114 as follows:

```
4 3 3 3 2 1 2 7 2 2 2 5 5 1 2 5 3 2 2 1 1 1 1 10 2 6 1 1 1 5 4 2 1 2 1 1 2 3 2 1 4 1 2 6 3 2 1 2 1 2 2 1 1 1 4 1 1 1
1 1 3 1 3 2 1 2 1 3 1 2 5 1 1 5 1 3 2 1 1 1 2 3 2 4 5 1 1 1 4 2 1 3 2 1 2 2 2 2 2 1 8 2 1 1 1 3 1 4 2 2 1 1 2 2 3 2 2
1 2 1 1 5 1 1 3 2 1 2 6 1 4 2 1 2 1 1 1 1 3 1 1 1 1 3 1 1 1 1 1 4 5 2 1 4 8 1 3 1 1 1 3 2 9 2 1 5 5 1 1 2 5 3 2 2 1 1
1 1 10 2 6 1 1 1 3 1 2 1 4 1 6 4 2 2 3 2 3 3 5 2 4 2 5 5 2 5 2 1 2 1 2 2 2 2 1 6 1 1 8 2 1 6 2 1 5 5 2 3 1 2 1 6 1 2
3 2 4 3 5 1 4 8 3 2 7 2 2 1 4 2 1 1 2 2 3 3 1 1 4 2 1 6 8 1 1 5 1 1 1 2 2 3 3 2 3 1 10 3 1 4 1 1 2 2 3 1 1 2 3 1 2 1
3 6 1 2 2 5 2 4 6 2 2 2 2 2 4 6 1 2 3 3 1 2 4 4 8 10 6 7 3 1 1 1 3 1 6 2 4 3 2 5 1 2 2 3 1 2 6 1 1 1 4 6 1 1 1 4 1 2
1 1 1 3 3 1 1 4 2 2 1 2 1 1 2 4 2 1 3 2 1 2 2 1 2 3 1 1 1 1 6 1 3 3 1 3 1 2 3 1 1 2 1 2 1 2 1 1 1 3 2 3 2 3 1 1 4 1 1
1 3 1 3 4 1 3 1 2 1 3 1 1 2 1 1 1 2 1 2 4 1 1 2 3 1 1 1 1 1 2 1 3 2 3 3 3 5 1 1 7 1 2 3 3 1 3 1 1 3 1 5 5 3 2 5 1 1 2
2 1 4 1 4 5 6 3 4 3 2 3 1 1 3 1 1 4 5 1 6 1 1 1 2 1 1 3 1 3 2 1 2 2 1 1 2 4 1 3 1 2 1 1 2 1 1 1 2 3 2 1 4 1 6 1 1 3 2
1 1 2 2 1 2 1 2 1 2 2 4 2 1 1 4 1 1 1 5 2 3 1 1 1 3 1 2 1 1 1 4 5 2 2 3 2 1 1 1 1 1 1 5 4 1 1 5 3
```

The sequence compression module 114 may store the first character file and the second character file as the most-frequent character files in the compression data 120. In one implementation, the first character file and the second character file may be converted into unary coded formats before being stored as the most-frequent character files. Further, the sequence compression module 114 may remove the current most-frequent character from the intermediate file to generate a least-frequent characters file having only the least-frequent characters. In an example, the least-frequent characters file thus generated is a binary file having the least-frequent characters. Referring back to the above example, the sequence compression module 114 may remove the current most-frequent character from the intermediate file to obtain the least-frequent characters file as follows (SEQ. ID NO.5):

The sequence compression module 114 may subsequently store the least-frequent characters file in a binary encoded (bit-stream) format in the compression data 120. For example, the sequence compression module 114 may store the least-frequent characters as a bit with value '0' or '1'.

In another embodiment of genomic data compression, the sequence compression module 114 analyzes the modified genomic data to identify absolute positions of the most-frequent character and the second most-frequent character in the modified genomic data. The sequence compression module 114 may compute a delta difference between successive positions of the two most-frequent characters to generate a positions file having the delta difference.

Referring to above discussed example, the sequence compression module 114 may analyze the modified genomic data to identify the absolute positions of the most-frequent character 'G' and the second most-frequent character 'C' as follows:

TAATTTAAAATTATAATATATAAATTTTAATATTAATTATATATTAAATTTTTTATAAAAATTTTTAAAATTTTA

TAATTAATTTTTAATAAAATATAAATAAATATTATTTTATAATTATTAAAATTAAATATAAAATAATATATAAAT

ATTTATATTAATAAATAAAAAAATAAAAATAATTAATATTAAATTATAATTATAAATTTTAATATTAATTATATA

TTAAATTTTTTATATTTTATTTATAAAATTAATATAATTAAATAAATTATATAAAATATTTTATTTATATAATT

TTAATTATTAATTATAAAATTTTTAAAAAAAATTTTATAAAAAATTTATATTATTTTATATTAATTAAATAATT

TAATTAAATAAATAAATATTTTTTAATTTTTTTTATTTTTAATAATATAATATATTTTATTTAAAAAATTTAAAT

TTTATAAATATTTAATATATATTATATTTATATTAAAAATAAAAAAAAAAAAAAAAAAAAAAAAAAAAAAAAAAA

AAAAAAAAAAAAAAAAAAAAAAAAAAAAAAAAAAAATATAATATAAATATATATATATTTAATATATATAAATTT

AATTTTAAAATAAATTTATTATTTAAAATTTTATAATTTTAATTTATATTTAATAATATTAAAAAAAATAAAATT

AATAAAATAATAATTTAAAAATAAATTAAAAAATTAATAATTAAATTTATTAAATTTTTTTAAATATTTATATA

ATTTAAATTTTTAAATAAATAATTAAAAAAAATTATTTAAAATATTTATTTATTTTTAAATTTAATAAAAATAAA

AATTTAATATTTTTATTAT 2 3 4 5 8 9 10 11 12 15 16 17 18 21 22 24 25 26 27 29 30 31 34 39 40 42 44 46 51 52 53 54 55 60 61 62 63 64 66 69 72 73 76 77 79 80 82 83 84 85 86 87 88 89 90 92 94 96 99 100 105 107 108 110 115 116 117 118 119 122 123 124 125 128 132 134 135 137 138 139 140 141 142 143 144 146 147 150 152 153 154 155 156 158 161 162 164 165 167 168 171 172 173 174 175 177 179 180 182 183 184 186 187 188 189 191 192 194 195 197 198 200 201 202 203 204 207 208 210 211 212 213 214 215 216 217 218 221 222 223 224 227 228 230 231 232 234 235 236 237 240 241 242 243 244 245 246 248 249 252 255 256 257 258 259 260 261 264 266 267 269 270 271 272 273 276 278 279 280 281 282 284 286 288 289 290 291 293 294 297 298 299 300 301 303 308 309 310 311 312 313 314 315 317 320 321 323 324 325 326 327 330 332 333 335 336 338 339 341 342 343 345 346 348 349 350 351 353 354 357 360 363 365 366 367 368 369 370 371 374 375 378 380 381 383 384 386 387 388 389 391 392 394 395 398 399 400 402 404 405 406 407 408 410 411 412 414 417 419 420 421 422 423 424 425 428 429 431 432 433 434 435 437 438 443 444 446 447 449 452 453 455 456 458 459 460 461 462 463 464 467 468 469 470 471 472 473 474 475 476 477 478 479 480 483 484 485 486 487 488 489 490 494 499 501 502 503 504 508 509 513 515 519 520 521 522 523 524 525 526 528 530 531 532 533 534 537 539 540 542 543 546 551 553 555 556 561 562 563 564 565 570 571 572 573 574 575 577 580 583 584 587 588 590 591 593 594 595 596 597 598 599 600 601 603 605 607 610 611 616 618 619 621 626 627 628 629 630 633 634 636 637 638 642 643 648 649 651 654 655 657 659 661 662 665 667 670 671 674 677 680 682 684 687 689 692 695 700 702 704 705 706 710 711 713 714 715 716 717 718 720 721 723 724 725 727 729 730 731 732 734 735 736 737 741 742 744 745 746 748 749 750 751 752 756 761 762 763 765 766 767 768 769 770 774 776 777 779 780 781 783 784 788 794 800 802 805 808 809 811 814 815 817 818 819 820 822 824 828 829 830 832 833 836 837 839 840 843 845 848 850 852 855 856 860 861 865 870 873 874 876 883 885 887 888 892 894 895 896 897 898 899 901 902 903 904 906 909 912 913 914 915 916 920 921 923 924 930 932 934 935 936 939 943 944 945 948 949 952 953 954 955 957 959 962 965 967 970 971 973 975 976 980 982 986 987 988 990 992 993 994 997 999 1000 1001 1002 1003 1004 1006 1007 1009 1010 1013 1014 1015 1017 1018 1021 1022 1023 1025 1026 1027 1030 1031 1032 1033 1035 1040 1041 1042 1044 1045 1046 1048 1051 1052 1054 1056 1058 1062 1063 1064 1065 1066 1072 1074 1075 1077 1079 1081 1082 1083 1084 1085 1087 1088 1092 1095 1096 1097 1101 1102 1103 1105 1106 1109 1110 1113 1114 1116 1117 1118 1120 1123 1124 1128 1129 1132 1134 1139 1144 1146 1148 1152 1153 1160 1222 1223 1224 1225 1227 1228 1230 1232 1233 1234 1235 1236 1237 1238 1239 1242 1243 1247 1248 1250 1257 1263 1265 1266 1270 1271 1274 1276 1277 1280 1281 1284 1285 1286 1288 1289 1291 1292 1293 1296 1297 1299 1302 1306 1307 1308 1309 1310 1311 1312 1313 1315 1317 1319 1320 1322 1323 1328 1329 1330 1331 1332 1335 1337 1338 1339 1341 1342 1343 1344 1345 1346 1347 1350 1353 1354 1355 1356 1359 1361 1362 1363 1364 1366 1367 1369 1370 1371 1373 1374 1375 1376 1377 1378 1380 1382 1385 1386 1388 1389 1390 1391 1394 1396 1397 1398 1400 1402 1403 1405 1406 1407 1408 1411 1412 1413 1414 1415 1416 1417 1418 1424 1425 1427 1428 1429 1431 1433 1435 1436 1439 1440 1441 1443 1444 1447 1448 1449 1450 1451 1453 1454 1455 1457 1458 1459 1460 1461 1463 1464 1465 1466 1467 1469 1470 1472 1473 1474 1476 1479 1480 1481 1482 1484 1487 1488 1489 1490 1491 1492 1493 1494 1496 1499 1500 1501 1502 1503 1505 1506 1508 1509 1510 1511 1514 1515 1516 1517 1518 1522 1523 1526 1527 1529 1530 1531 1532 1535 1536 1537 1538 1540 1541 1542 1543 1544 1545 1547 1548 1549 1550 1551 1553 1554 1555 1557 1560 1561 1562 1563 1565 1568 1569 1570 1571 1572 1573 1574 1575 1576 1577 1579 1580 1583 1584 1586 1589 1592 1595 1599 1601 1602 1603 1607 1608 1612 1613 1614 1615 1616 1618 1620 1621 1623 1626 1627 1629 1631 1632 1633 1634 1635 1636 1639 1640 1642 1644 1645 1648 1650 1653 1655 1656 1659 1660 1662 1666 1668 1669 1670 1671 1672 1674 1676 1677 1678 1682 1683 1684 1685 1686 1687 1688 1689 1690 1691 1695 1697 1701 1702 1703 1706 1709 1710 1711 1713 1715 1717 1720 1722 1723 1724 1725 1727 1729 1730 1731 1733 1736 1737 1738 1739 1740 1741 1742 1743 1746 1747 1748 1749 1750 1751 1752 1754 1757 1758 1762 1764 1765 1766 1767 1771 1774 1775 1776 1777 1778 1780 1781 1782 1783 1786 1787 1788 1789 1790 1793 1795 1796 1798 1799 1800 1802 1803 1804 1805 1806 1808 1810 1813 1814 1815 1816 1817 1818 1820 1822 1823 1825 1826 1827 1828 1829 1831 1832 1833 1834 1835 1836 1837 1838 1840 1841 1844 1846 1847 1848 1849 1852 1854 1855 1861 1862 1863 1865 1867 1868 1870 1871 1872 1873 1874 1875 1877 1879 1880 1881 1882 1883 1885 1886 1887 1889 1890 1892 1893 1894 1895 1897 1898 1899 1900 1904 1905 1907 1908 1909 1910 1911 1915 1916 1917 1918 1919 1922 1925 1926 1928 1931 1932 1933 1934 1935 1938 1939 1940 1941 1942 1944 1945 1946 1947 1948 1949 1950 1951 1952 1954 1955 1956 1959 1960 1961 1966 1967 1968 1969 1970 1972 1973 1975 1978 1979 1980 1982 1983 1984 1985 1986 1987 1988 1989 1990 1991 1994 1997 2001 2002 2003 2005 2008 2010 2011 2014

The positions file having the delta difference may then be generated by the sequence compression module 114 as follows:

2 1 1 1 3 1 1 1 1 3 1 1 1 3 1 2 1 1 1 2 1 1 3 5 1 2 2 2 5 1 1 1 1 5 1 1 1 1 2 3 3 1 3 1 2 1 2 1 1 1 1 1 1 1 1 2 2 2 3
1 5 2 1 2 5 1 1 1 1 3 1 1 1 3 4 2 1 2 1 1 1 1 1 1 1 2 1 3 2 1 1 1 1 2 3 1 2 1 2 1 3 1 1 1 1 2 2 1 2 1 1 2 1 1 1 2 1 2
1 2 1 2 1 1 1 1 3 1 2 1 1 1 1 1 1 1 3 1 1 1 3 1 2 1 1 2 1 1 1 3 1 1 1 1 1 1 1 1 1 3 1 2 1 2 1 1 1 1 3 2
1 1 1 1 2 2 2 1 1 1 2 1 3 1 1 1 1 2 5 1 1 1 1 1 1 1 2 3 1 2 1 1 1 1 1 3 2 1 2 1 2 1 2 1 1 2 1 2 1 1 1 2 1 3 3 3 2 1 1 1
1 1 1 3 1 3 2 1 2 1 2 1 1 1 2 1 2 1 3 1 1 2 2 1 1 1 1 2 1 1 2 3 2 1 1 1 1 1 3 1 2 1 1 1 1 2 1 5 1 2 1 2 3 1 2 1 2 1
1 1 1 1 1 3 1 1 1 1 1 1 1 1 1 1 1 1 1 3 1 1 1 1 1 1 1 4 5 2 1 1 1 4 1 4 2 4 1 1 1 1 1 1 1 2 2 1 1 1 1 3 2 1 2 1 3 5 2
2 1 5 1 1 1 1 5 1 1 1 1 1 2 3 3 1 3 1 2 1 2 1 1 1 1 1 1 1 1 2 2 2 3 1 3 2 1 1 1 1 3 1 2 1 1 1 4 1 5 1 2 3 1 2 2 2
1 3 2 3 1 3 3 3 2 2 3 2 3 3 5 2 2 1 1 4 1 2 1 1 1 1 1 2 1 2 1 1 2 2 1 1 1 2 1 1 1 4 1 2 1 1 2 1 1 1 1 4 5 1 1 2 1 1 1
1 1 4 2 1 2 1 1 1 2 1 4 6 6 2 3 3 1 2 3 1 2 1 1 1 1 2 2 4 1 1 2 1 3 1 2 1 3 2 3 2 2 2 3 1 4 1 4 5 3 1 2 7 2 2 1 4 2 1 1 1 1
1 2 1 1 2 3 3 1 1 1 1 4 1 2 1 6 2 2 1 1 3 4 1 1 3 1 3 1 1 1 2 2 3 3 2 3 1 2 2 1 4 2 4 1 1 2 2 1 1 3 2 1 1 1 1 2 1
2 1 3 1 1 2 1 3 1 1 2 1 1 3 1 1 1 2 5 1 1 2 1 1 2 3 1 2 2 2 4 1 1 1 1 6 2 1 2 2 2 1 1 1 1 1 2 1 4 3 1 1 4 1 1 2 1 3 1 3
1 2 1 1 2 3 1 4 1 3 2 5 5 2 2 4 1 7 6 2 1 1 1 2 1 2 2 2 1 1 1 1 1 1 1 1 3 1 4 1 2 7 6 2 1 4 1 3 2 1 3 1 3 1 1 2 1 2 1 1 3
1 2 3 4 1 1 1 1 1 1 1 1 2 2 2 1 2 1 5 1 1 1 1 3 2 1 1 2 1 1 1 1 1 1 3 1 1 3 2 1 1 1 3 1 1 1 1 2 1 2 1 1 1 1 2 1 1 1 1 2 2 3 1 2
1 1 1 3 2 1 1 2 2 1 2 1 1 3 1 1 1 1 1 1 1 6 1 2 1 2 2 2 1 3 1 1 2 1 3 1 1 1 1 2 1 1 2 1 1 1 1 1 2 1 1 1 1 1 1 2 1 1
2 3 1 1 1 2 3 1 1 1 1 1 1 1 2 3 1 1 1 1 1 2 1 2 1 1 1 3 1 1 1 1 4 1 3 1 2 1 1 1 3 1 1 1 2 1 1 1 1 1 2 1 1 1 1 1 2 1 1 2 3
1 1 1 2 3 1 1 1 1 1 1 1 1 1 2 1 3 1 2 3 3 3 4 2 1 1 4 1 4 1 1 1 1 2 2 1 2 3 1 2 2 1 1 1 1 1 3 1 2 2 1 3 2 3 2 1 3 1 2
4 2 1 1 1 1 2 2 1 1 4 1 1 1 1 1 1 1 1 1 4 2 4 1 1 3 3 1 1 2 2 2 3 2 1 1 1 1 2 2 1 1 2 3 1 1 1 1 1 1 1 3 1 1 1 1 1 1 2 3
1 4 2 1 1 1 1 4 3 1 1 1 1 1 2 1 1 1 3 1 1 1 1 1 3 2 1 2 1 1 1 2 1 1 1 1 1 2 2 3 1 1 1 1 1 1 2 2 1 2 1 1 1 1 1 1 2 1 1 1 1 1 1 1 1 1 2 1 3

2 1 1 1 3 2 1 6 1 1 2 2 1 2 1 1 1 1 1 2 2 1 1 1 1 2 1 1 2 1 2 1 1 1 2 1 1 1 4 1 2 1 1 1 1 4 1 1 1 1 3 3 1 2 3 1 1 1 1
3 1 1 1 1 2 1 1 1 1 1 1 1 1 2 1 1 3 1 1 5 1 1 1 1 2 1 2 3 1 1 2 1 1 1 1 1 1 1 1 1 3 3 4 1 1 2 3 2 1 3

The sequence compression module 114 may further determine the order of occurrence of the most-frequent character and the second most-frequent character based on the positions file to generate an occurrence file. The occurrence file may be understood as a binary file having the most-frequent character and the second most-frequent character in the order of their occurrence in the modified genomic data.

Referring back to the above mentioned example, the sequence compression module 114 may generate the occurrence file as follows (SEQ. ID NO.6):

one implementation, the positions file may be converted into a unary coded format, while the occurrence file may be stored in a binary encoded, i.e., bit-stream format before being saved as the most-frequent character files. Further, the sequence compression module 114 removes the most-frequent character and the second most-frequent character from the modified genomic data to generate the least-frequent characters file.

In the example discussed previously, the sequence compression module 114 may remove the most-frequent charac-

GGGGCGGGGCGGCGCGGCGGCGCGCCCGGGCGGGGCCCGGCGCCGGCGGCCGCCGGGGGCG

CGCGCCCGGGGCCCCGCCGGGCGCGCGGCCGGCCGCGGGGGGGCGGGGGCGGCCCCGCCGCC

CGGGCCCGCGCCGCGCCGCCGGCCGGCCGGGGCGGGCCGGCGGGGCGCGGCCGCCCCGCGGGC

GGGGGGCCGGCGGCCGCGCCGGGCCCCGCGCGGCGGGCCGGGGCCGCCCGGCCGGCGCCGCCC

GCGGGCCGCGGCCCCGGCGCGCGGCGGGCCGCGGGCCGCGCCCCCGGCGGCGGCGGCCGCGG

GCCGCCCCCGCCGGCGGGCGCGGGGGCCCCCGCGGGGCCCGGCGGGGCCCCGGCGCCGGC

GGCCGCCGGGGCGCGCGCCCCCGCCCGGCGGCCGCCCCGCGCCGCCGCCCGGGCGGGCCGG

CCGCGCGGGCCGCGGGGGGCGCCGGCGGGCGGGCGGGGGCGCGGCGGCCCCGGCCGGCGCG

CGCCGGCCGGCCGCGCCGCCCCCCGGCGCGCGGCCGCGCCCGCCCGGGGGCCCGGCCCCCCC

CCCGGGGGGGCGCGCGGCGCGCCGCCCGCGCCCGCGCGGGGCCGCGCGGGCCGGGCGCGCC

CGGCGGCGCGGGCCGGCCGCCGGCGGCGCGGCGGGGCGGCCCCGGGCGGCGCCGCGGGGCGCG

CCGCGGCCGGCCGGCCCGCGGCCGCCGGGCGGCGCCCGCGCGGCCGCCCCGCCGCGGGCGCCG

CGCGCGCGCGCGGCCCCGCCCGGGCGGCCGCCCGGGCGCCCCGCGCGCGCCCGCGCGGCGC

CCGGGGCCGGCGCCGGCGGCGGCGCCCGGCGGCGGGCGCCCCGGCCGCCCCGCCGCGGCGGC

GGCCGCCCCGCGCGCGCCCGCCCCGCCCGGGCCGGCGGCCCGCCGGCGCCGGGCGGCGCGCG

CGCCGCCCGGGGGCGGCGCGGCGGGGGCGCGGCGGGCGGCCGGCGGGCGGCGCGCGCGGCG

GCGCCGCCCGCCGCGCGCCCCGGCGCCGCGGGGCGCGCCCCGCGCGCGGCCGCCGGCCGCCC

CCGCGCCGGCGCCGGCGCGCCCGCGGGGGCGCCGGCCCCCGGCGCCCCGCGCGCGCCGGCGG

GCGGGGCGGGGCGCGCGCGCGCCGCCCCGGCCCCGGCGC

The positions file and the occurrence file subsequently may be saved by the sequence compression module 114 as the most-frequent character files in the compression data 120. In ter and the second most-frequent character from the modified genomic data to obtain the least-frequent characters file as follows (SEQ. ID NO.7):

TAATTTAAAATTATAATATATAAATTTTAATATTAATTATATATTAAATTTTTTATAAAAATTTTTAAAATTTTA

TAATTAATTTTTAATAAAATATAAATAAATATTATTTTATAATTATTAAAATTAAATATAAAATAATATATAAAT

ATTTATATTAATAAATAAAAAAATAAAAATAATTAATATTAAATTATAATTATAAATTTTAATATTAATTATATA

TTAAATTTTTTATATTTTATTTATAAAATTAATATAATTAAATAAATTATATAAAATATTTTATTTATATAATTT

TTAATTATTAATTATAAAATTTTTAAAAAAAATTTTATAAAAAAATTTATATTATTTTATATTAATTAAATAATT

TAATTAAATAAATAAATATTTTTTAATTTTTTTTATTTTTAATAATATAATATATTTTATTTAAAAAATTTAAAT

TTTATAAAATATTTAATATATATTATATTTATATTAAAAATAAAAAAAAAAAAAAAAAAAAAAAAAAAAAAAAAA

AAAAAAAAAAAAAAAAAAAAAAAAAAAAAAAAAAAAAATATAATATAAATATATATATATTTAATATATATAAATTT

```
-continued
AATTTTAAAATAAATTTATTATTTAAAATTTTATAATTTTAATTTATATTTAATAATATTAAAAAAAATAAAATT

AATAAAATAATAATTTAAAAATAAATTAAAAAATTAATAATTAAATTTATTAAATTTTTTTAAATATTTATATA

ATTTAAATTTTTAAATAAATAATTAAAAAAAATTATTTAAAATATTTATTTATTTTTAAATTTAATAAAAATAAA

AATTTAATATTTTTATTAT
```

Further, the sequence compression module 114 may store the least-frequent characters file in a binary encoded, i.e., bit-stream format in the compression data 120.

The least-frequent characters file, the most-frequent character files, and the intermediary data obtained using either of the embodiments thus provide the compressed genomic data and may be used for further processing or storage. Further, in order to facilitate an efficient processing and storing, the sequence compression module 114 may archive the least-frequent characters file, the most-frequent character files, and the intermediary data together to generate a final output file, referred to as the compressed genomic data. As will be understood by a person skilled in the art, the sequence compression module 114 may use any known archiving or compression technology, such as Zip technology implementing various technologies, such as DEFLATE, LZMA, and BZIP for producing the compressed genomic data.

Validation and Results

For the purpose of validation, four different types of genomic data sets were obtained and compressed using the system 100 in accordance with both the embodiments. The results were further compared with conventional techniques, such as GZIP—version 1.4, and LZMA—version 9.20. The experiments were performed using a desktop having a dual core 2.33 gigahertz (Ghz) processor with 2 gigabytes (GB) RAM. The system 100 and the conventional techniques were used to compress the four genomic data sets and their results were evaluated using the compression ratio achieved by all the techniques and the time taken for compression and decompression. In one implementation, the compression ratio may be understood as a percentage ratio of the compressed file size and the size of the original file having the genomic data.

The experiments were conducted using four data sets, viz., prokaryotic genomes, prokaryotic gene annotation files, eukaryotic genomes (Human chromosomes), and metagenomic data sets. The prokaryotic genomes data set included 2679 FNA files, downloaded from the NCBI database, corresponding to completely sequenced prokaryotic genomes along with corresponding plasmid sequences. The size of the individual FNA files varied from about 1393 bytes to about 12.6 MB. The Prokaryotic gene annotation files data set included 2679 FFN files, downloaded from the NCBI database, corresponding to annotated gene sequences corresponding to completely sequenced prokaryotic genomes. The size of these FFN files varied between 823 bytes to approximately 11.8 MB. Further, the eukaryotic genomes data set files correspond to 25 human chromosomes (chromosomes 1-22, M, X and Y; Build 36.1, hg18, March 2006). The files used for performance evaluation were downloaded from UCSC website (http://hgdownload.cse.ucsc.edu/goldenPath/hg18/chromosomes/). The eukaryotic genomes data set besides containing several stretches of non-ATGC characters, contained repetitive regions within these chromosome files. The repetitive regions within these chromosome files were indicated in lower-case characters. The metagenomic data sets corresponding to 14 metagenomes were downloaded from the CAMERA web-portal. The size of the metagenomes varied in size from about 3.3 MB to about 4.2 GB.

Results obtained after compression of the various genomic data sets using the system 100 and the conventional techniques are summarized in table 1.

TABLE 1

| Validation data set | Size of original data set (in bytes) | Compressed file size (in bytes) (Compression ratio is indicated in brackets) | | | | | |
|---|---|---|---|---|---|---|---|
| | | First Embodiment | Second Embodiment | BZIP2 | GZIP (Default) | GZIP (with-9 option) | LZMA (7ZIP) |
| 2679 Prokaryotic genome files [.fna files] | 5313431620 | 1280304032 [24.1] | 1278711471 [24.07] | 1483465009 [27.92] | 1594820733 [30.01] | 1533913312 [28.87] | 1400734703 [26.36] |
| 2679 Prokaryotic gene annotation files [.ffn files] | 5069754176 | 1165274782 [22.98] | 1164724778 [22.97] | 1339731298 [26.43] | 1525422082 [30.09] | 1470442823 [29] | 1283932603 [25.33] |
| Eukaryotes [25 Human chromosomes] | 3142044948 | 680305450 [21.65] | 659696075 [21] | 807744829 [25.71] | 876870040 [27.91] | 841024949 [26.77] | 719817274 [22.91] |
| 14 Metagenomic data sets | 9265470641 | 1178241190 [12.72] | 1146241066 [12.37] | 1542436155 [16.65] | 1927069056 [20.8] | 1847077414 [19.94] | 1258839496 [13.59] |
| TOTAL | 22790701385 | 4304125454 [20.36] | 4249373390 [20.1] | 3630941136 [24.18] | 5924181911 [27.2] | 5692458498 [26.78] | 4563324076 [22.05] |

Table 1 indicates size of the final compressed files for the various techniques. Further, the compression ratios corresponding to each of the compression technique are indicated in parenthesis.

The compression ratios obtained using both the embodiments of the system 100 may be compared to obtain a percentage improvement in compression ratio over conventional techniques for each genomic data set. The percentage improvement may be understood as a percentage gain in the compression ratio achieved using the system 100 over the compression ratio achieved using the conventional techniques. Percentage improvements according to the first embodiment and the second embodiment with respect to the results obtained using the conventional techniques are depicted in tables 2 and 3, respectively.

TABLE 2

| Validation data set | Percentage improvement in compression ratio achieved using First embodiment | | | |
|---|---|---|---|---|
| | BZIP2 | GZIP (default) | GZIP (with −9 option) | LZMA (7ZIP) |
| Prokaryotic FNA files | 13.7 | 19.72 | 16.53 | 8.6 |
| Prokaryotic FFN files | 13.02 | 23.61 | 20.75 | 9.24 |
| Eukaryotic chromosomes | 15.78 | 22.42 | 19.11 | 5.49 |
| Metagenomes | 23.61 | 38.86 | 36.21 | 6.4 |
| Average | 16.53 | 26.15 | 23.15 | 7.43 |

TABLE 3

| Validation data set | Percentage improvement in compression ratio achieved using Second embodiment | | | |
|---|---|---|---|---|
| | BZIP2 | GZIP (default) | GZIP (with −9 option) | LZMA (7ZIP) |
| Prokaryotic FNA files | 13.8 | 19.82 | 16.64 | 8.71 |
| Prokaryotic FFN files | 13.06 | 23.65 | 20.79 | 9.28 |
| Eukaryotic chromosomes | 18.33 | 24.77 | 21.56 | 8.35 |
| Metagenomes | 25.69 | 40.52 | 37.94 | 8.94 |
| Average | 17.72 | 27.19 | 24.23 | 8.82 |

As can be seen from the tables 1, 2, and 3 the compression ratio obtained using the two embodiments of the system 100 are approximately 8% to 25% (up to 40% in some cases) efficient as compared to the conventional techniques.

Further, the results of compression and decompression time using the system 100 and the conventional techniques are depicted in table 4.

Table 4 indicates total time taken, in seconds, for compression and decompression of the data sets using the various techniques. Further, compression and decompression time are separately indicated in parenthesis.

Figure 2A:
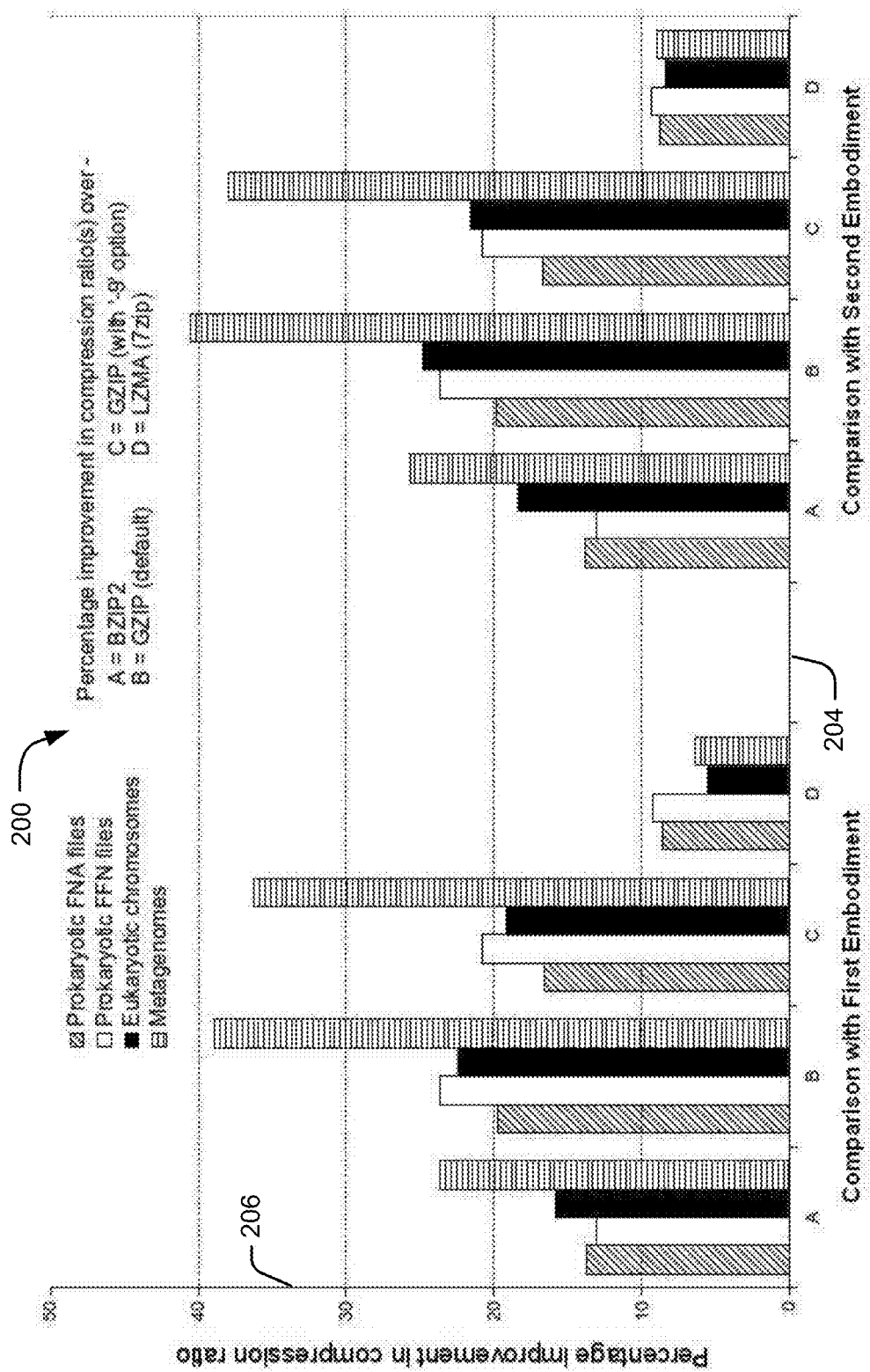
FIG. 2a illustrates a plot depicting compression ratios achieved using the system for compression of genomic data, according to an embodiment of the present subject matter and a comparison thereof when achieved using the conventional system for compression.
Figure 2B:
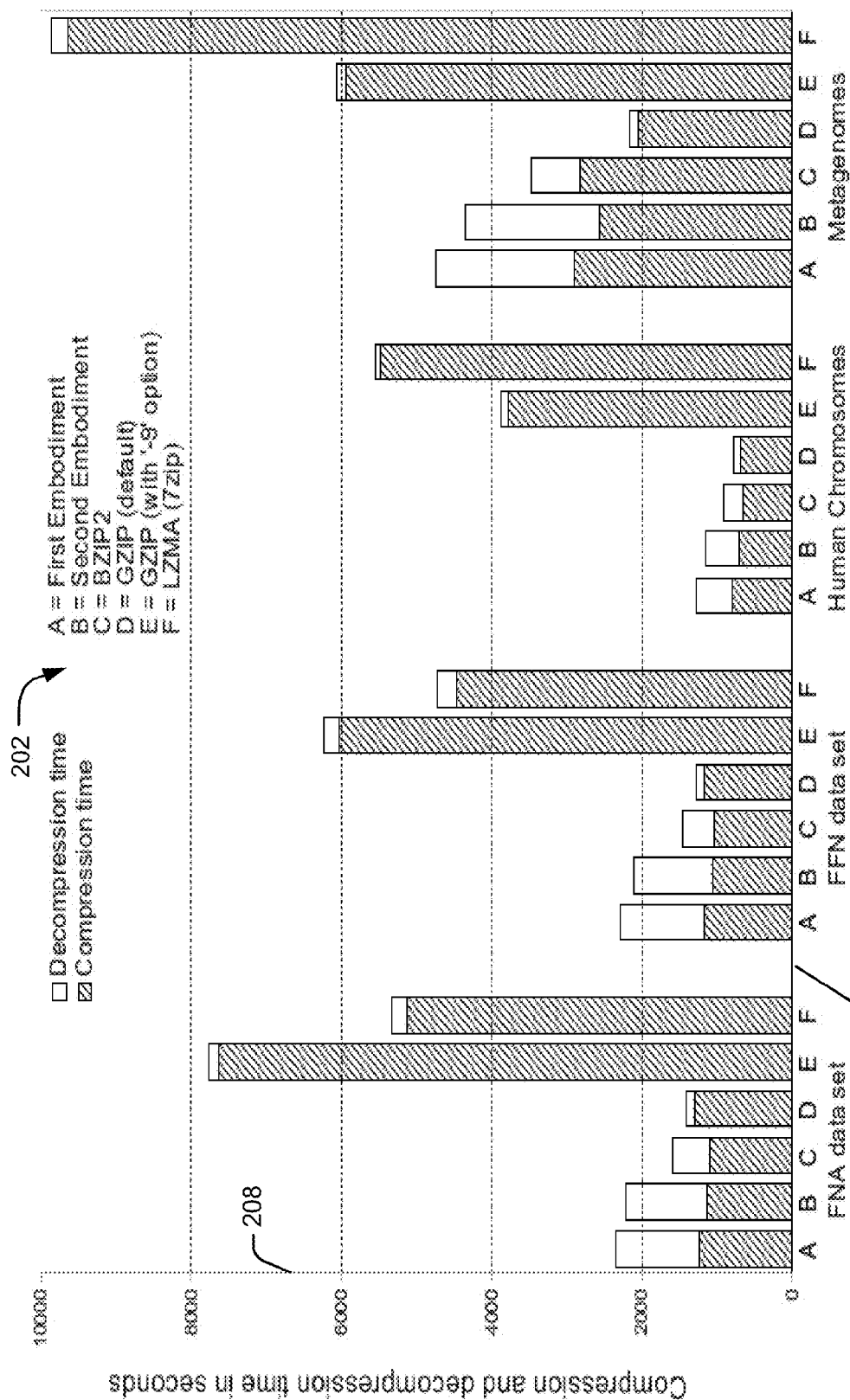
FIG. 2b illustrates a plot depicting compression and decompression time required using the system for compression of genomic data, according to an embodiment of the present subject matter and a comparison thereof when achieved using the conventional system for compression.

Further, the results of compression and decompression using the system 100 and the conventional techniques are depicted in bar plots 200 and 202 illustrated in FIGS. 2a and 2b. The plot 200 depicts a comparison of compression ratios obtained using the present subject matter and certain conventional techniques, such as BZIP2, GZIP (default), GZIP (with '−9' option), and LZMA (7zip). In the plot 200, the compression techniques used for compressing various data sets are represented on a horizontal axis 204. Further, percentage improvement according to the first embodiment and the second embodiment with respect to the results obtained using the conventional techniques is represented along a vertical axis 206. In one implementation, results obtained with input genomic data as prokaryotic FNA files are represented by diagonal lines, as prokaryotic FFN files are represented with white fill, as eukaryotic chromosomes are represented using black fill, and as Metagenomes are represented using horizontal lines.

Further, in the plot 200, BZIP2 is illustrated as 'A', GZIP (default) technique is illustrated as 'B', GZIP (with −9 option) technique is illustrated as 'C', and LZMA (7ZIP) technique is illustrated as 'D'. As illustrated in the plot 200, the compression ratio obtained using the two embodiments of the system 100 has improved in the range of about 6% to 40% as compared to the conventional techniques.

The plot 202 depicts a comparison of time taken for compression and decompression of data sets using the present subject matter and the conventional techniques. In the plot 202, the compression and decompression time, in seconds, is represented along a vertical axis 208, while various data sets being compressed and decompressed are represented on a horizontal axis 210. In one implementation, the data sets used for the comparison are prokaryotic FNA files, prokaryotic FFN files, eukaryotic chromosomes and metagenomes. The compression time taken by each of the techniques is represented by diagonal lines, while the decompression time taken by each of the techniques is represented by using white fill.

Further, compression and decompression time taken for each of the data sets by the first embodiment of the system 100 is illustrated as 'A', the second embodiment of the system 100 is illustrated as 'B', BZIP2 technique is illustrated as 'C', GZIP (default) technique is illustrated as 'D', GZIP (with −9 option) technique is illustrated as 'E', and LZMA (7ZIP) technique is illustrated as 'F'. As illustrated in the plot 202, the compression time achieved using the system 100 is almost similar to compression time required by GZIP (default) and

TABLE 4

| Data set | Size of original data set (in bytes) | Total time (in seconds) for compression and decompression (Compression time + Decompression time) | | | | | |
|---|---|---|---|---|---|---|---|
| | | First Embodiment | Second Embodiment | BZIP | GZIP (Default) | GZIP (with-9 option) | LZMA (7ZIP) |
| Prokaryotic FNA files | 5313431620 | 2347 (1238 + 1109) | 2219 (1134 + 1085) | 1582 (1097 + 485) | 1404 (1303 + 101) | 7756 (7639 + 117) | 5335 (5150 + 215) |
| Prokaryotic FFN files | 5069754176 | 2283 (1175 + 1108) | 2098 (1063 + 1035) | 1459 (1038 + 421) | 1268 (1165 + 103) | 6229 (6030 + 199) | 4715 (4461 + 254) |
| Eukaryotic Chromosomes | 3142044948 | 1276 (799 + 477) | 1156 (705 + 451) | 904 (651 + 253) | 785 (691 + 94) | 3872 (3781 + 91) | 5556 (5470 + 86) |
| Metagenomes | 9265470641 | 4741 (2897 + 1844) | 4349 (2566 + 1783) | 3475 (2823 + 652) | 2164 (2044 + 120) | 6064 (5945 + 119) | 9856 (9639 + 220) |

BZIP2 techniques. Further, the compression time required by the system 100 is significantly less than GZIP (−9 option) and the LZMA techniques. The decompression time achieved using the system 100, however, is more than the GZIP (−9 option) and the LZMA techniques.

Figure 3:
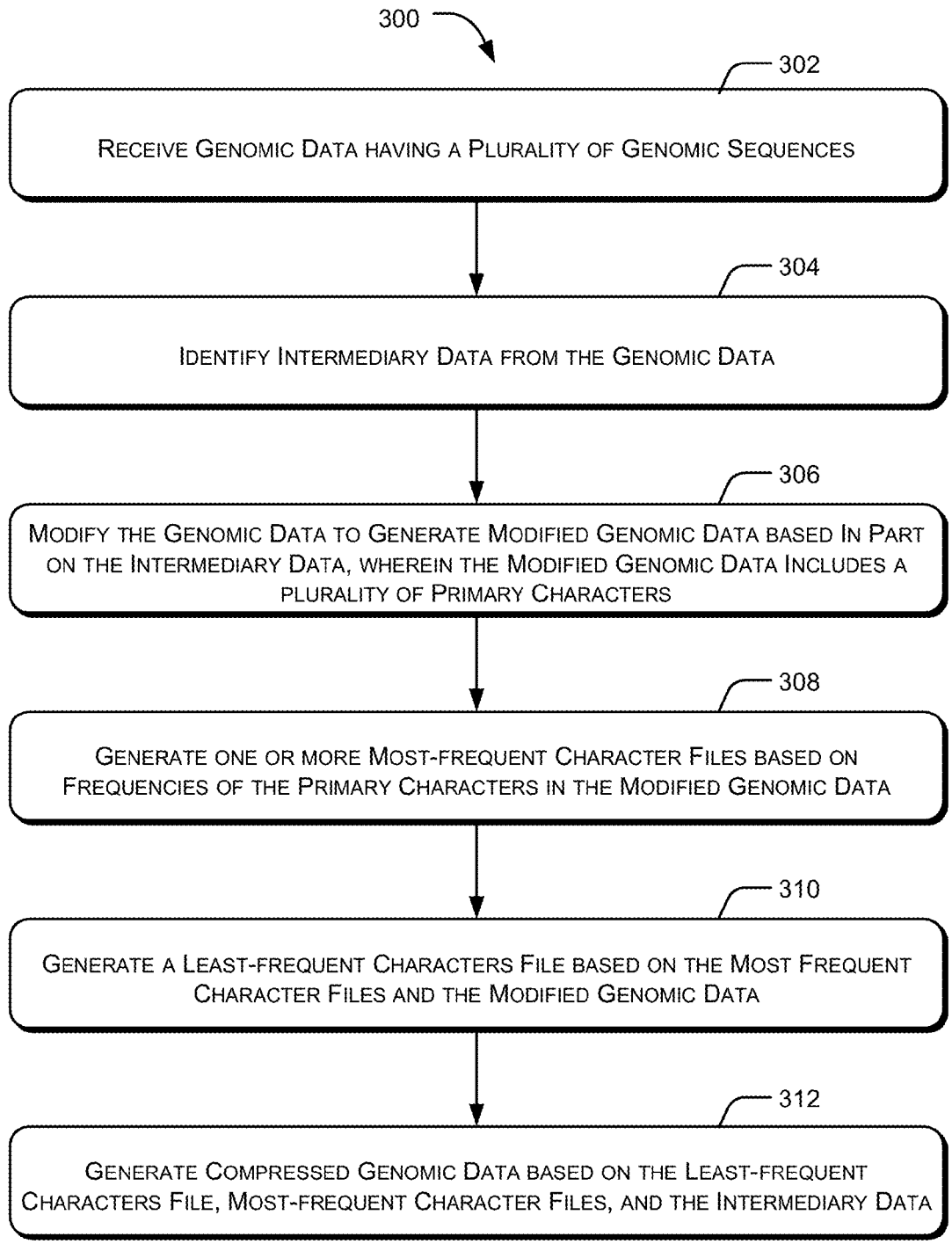
FIG. 3 illustrates a method for compression of genomic data, in accordance with an embodiment of the present subject matter.
Figure 4:
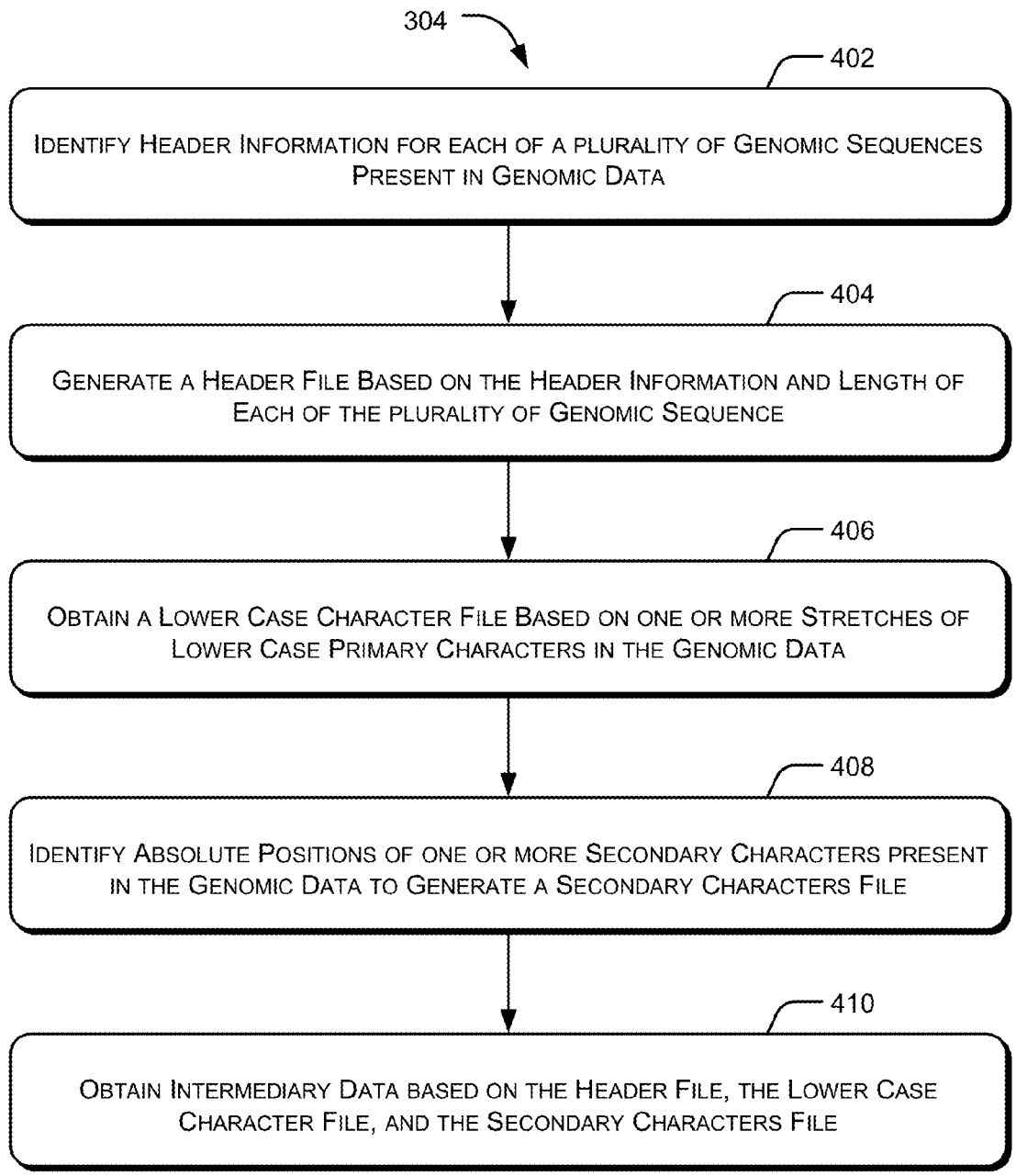
FIG. 4 illustrates a method for identifying intermediary data for modifying genomic data for compression, in accordance with an embodiment of the present subject matter.
Figure 5A:
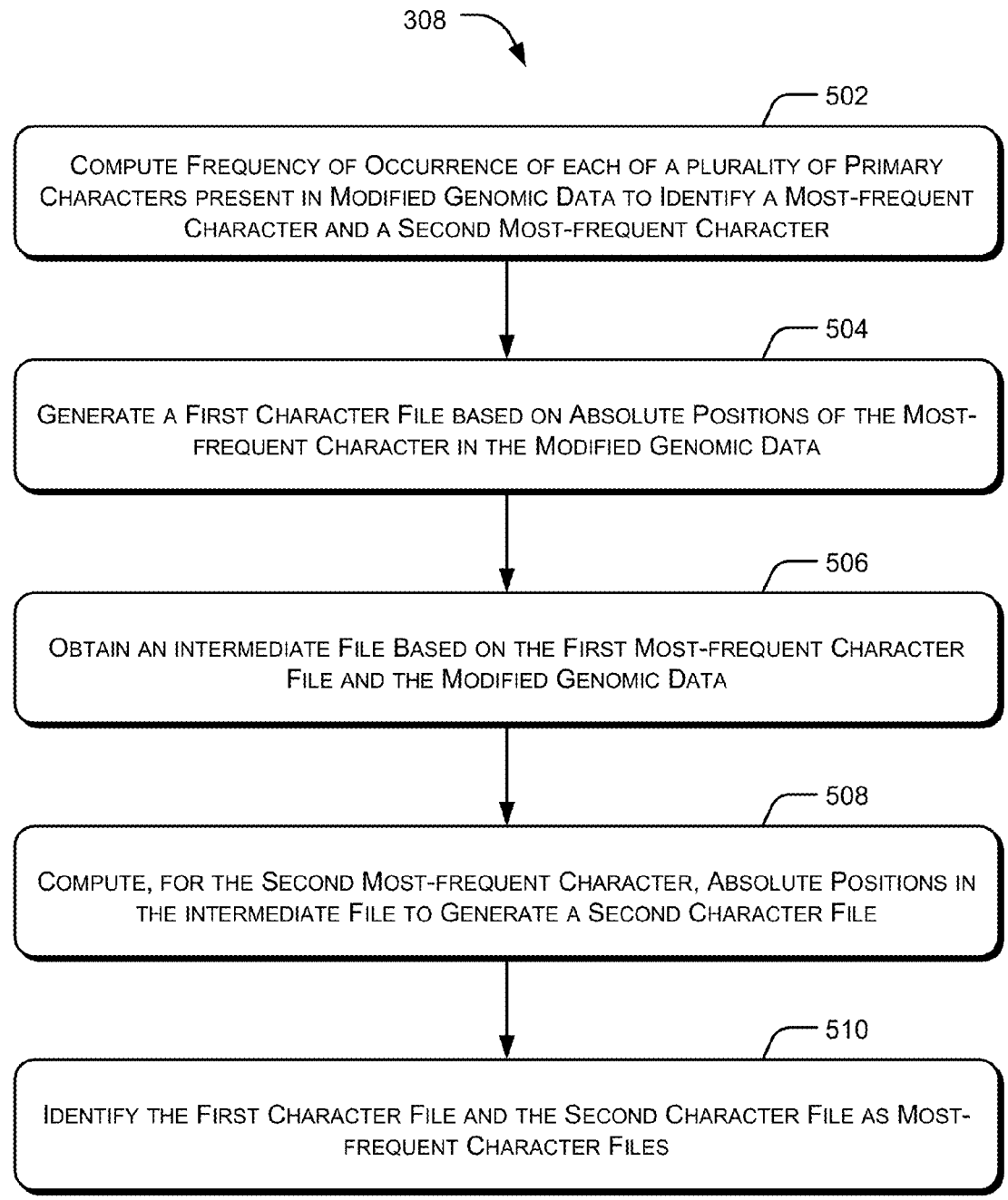
FIG. 5a illustrates a method of generating one or more most-frequent character files for compressing modified genomic data, in accordance with an embodiment of the present subject matter.
Figure 5B:
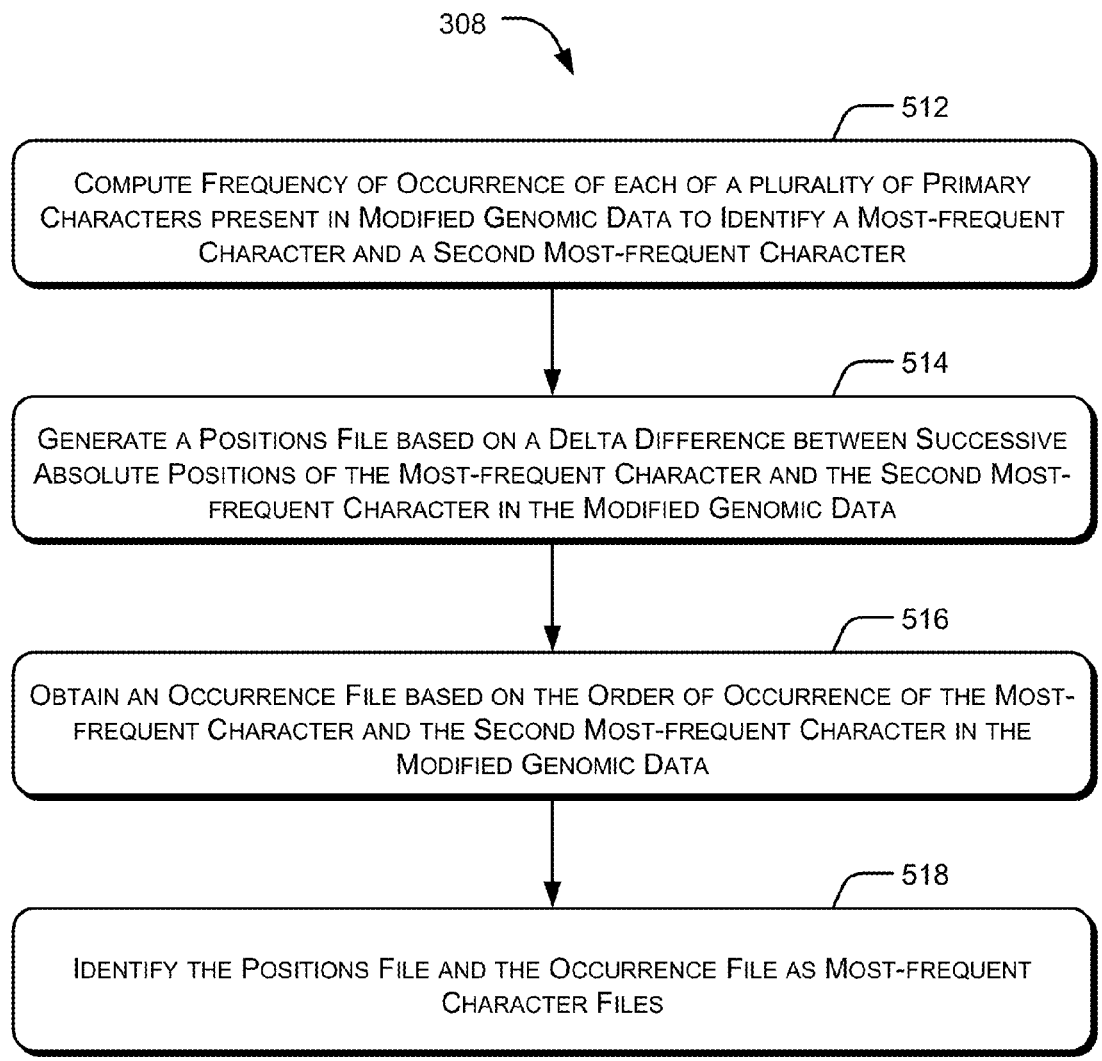
FIG. 5b illustrates a method of generating one or more most-frequent character files for compressing modified genomic data, in accordance with another embodiment of the present subject matter.

FIG. 3 illustrates a method 300 for compressing genomic data, in accordance with an implementation of the present subject matter, FIG. 4 illustrates a method 304 for modifying the genomic data for compression, FIG. 5a illustrates a method 308 for compressing the modified genomic data according to an embodiment, and FIG. 5b illustrates the method 308 for compressing the modified genomic data according to another embodiment. The methods 300, 304, and 308 are implemented in computing device, such as the genomic data compression system 100.

The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network.

The order in which the methods are described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the methods can be implemented in any suitable hardware, software, firmware, or combination thereof.

At block 302, genomic data, to be compressed, having a plurality of genomic sequences is received, for example, by the system. The genomic sequences may be, for example, nucleotide sequences, polypeptide sequences, DNA sequences, or RNA sequences. In an implementation, the genomic data may be stored in the input data 118.

At block 304, intermediary data included in the genomic data is identified. The intermediary data may include header information, secondary characters, and lower case characters in each of the genomic sequences. In an implementation, the sequence modification module 112 may identify the intermediary data.

At block 306, the genomic data may be modified to generate modified genomic data based in part on the intermediary data. The modified genomic data is generated such that it only includes a plurality of primary characters, as will be explained in detail with reference to FIG. 4. In an implementation, the sequence modification module 112 may generate the modified genomic data.

At block 308, one or more most-frequent character files are generated, based on frequencies of each of the primary characters in the modified genomic data. In an example, the most-frequent character files are generated based at least on a most-frequent character and a second most-frequent character from the primary characters, as will be explained in detail with reference to FIGS. 5a and 5b. In an implementation, the sequence compression module 114 generates the most-frequent character files.

At block 310, a least-frequent characters file is generated based on the most-frequent character files and the modified genomic data. The least-frequent characters file is a binary file and includes only the least-frequent characters from the primary characters present in the modified genomic data. In an implementation, the sequence compression module 114 generates the least-frequent characters file.

At block 312, compressed genomic data based on the least-frequent characters file, the most-frequent character files, and the intermediary data is generated. In one implementation, the sequence compression module 114 archives the least-frequent characters file, the most-frequent character files, and the intermediary data to produce the compressed genomic data. Further, the compressed genomic data may be archived using any known technique of archiving or compressing data. The compressed genomic data includes all the details pertaining to not only the primary characters but also the intermediary data. Thus, the described method provides for loss-less compression of data. Further, the genomic data is compressed without compromising on compression ratio and time, thereby making the described method efficient in terms of computational time and resources.

Referring to FIG. 4, the method 304 identifies intermediary data for modifying the genomic data to obtain modified genomic data for compression, in accordance with an embodiment of the present subject matter.

At block 402, genomic data, to be compressed, having a plurality of genomic sequences is analyzed for identifying header information associated with each of the sequences. In one implementation, the sequence modification module 112 is configured to identify the header information based on one or more preconfigured parameters or rules.

At block 404, a header file is generated based on the header information and length of each of the genomic sequences. In one implementation, the sequence modification module 112 identifies the length of the each of the genomic sequence and appends it with the corresponding header information to obtain the header file. The header file may then be saved in the compression data 120.

At block 406, a lower case character file is generated based one or more stretches of lower case primary characters present in the genomic data. The genomic data is analyzed, for example, by the sequence modification module 112 to identify all the primary characters present in the genomic data in lower case. A delta difference between adjacent positions of the stretches of lower case characters and the length of each of the stretches may then be computed to generate the lower case character file. The lower case character file may then be saved in the compression data 120 by the sequence modification module 112.

At block 408, absolute positions of one or more secondary characters present in the genomic data are identified to generate a secondary characters file. In one implementation, all the secondary characters present in the genomic data are identified by the sequence modification module 112. For example, genomic sequences, such as nucleotide sequences may include secondary characters, such as 'N', 'H', 'R', and 'S'. Based on the identification, absolute positions of the secondary characters may be determined and a delta difference between the absolute positions of adjacent secondary characters may be computed to generate the secondary characters file.

At block 410, intermediary data is obtained based on the header file, the lower case character file, and the secondary characters file. In one implementation, the sequence modification module 112 saves the header file, the lower case character file, and the secondary characters file as the intermediary data in the compression data 120.

Referring to FIG. 5a, the method 308 generates one or more most-frequent character files for compressing the modified genomic data, in accordance with an embodiment of the present subject matter.

At block 502, frequency of occurrence of each of a plurality of primary characters present in the modified genomic data is computed to identify a most-frequent character and a second most-frequent character. The modified genomic data is initially analyzed, for example, by the sequence compression module 114, to compute the frequency of occurrence of each of the primary characters. Based on the computation, the primary character having the highest frequency of occurrence may be identified as the most-frequent character and the primary character having the second highest frequency of occurrence may be identified as the second most-frequent character.

At block 504, a first character file is generated, for example, by the sequence compression module 114. In one implementation, modified genomic data is analyzed to determine the absolute positions of the most-frequent character. A delta difference between adjacent positions of the most-frequent character is subsequently computed to generate the first character file. In one example, the delta differences thus computed are unary coded in the first character file. In one implementation, the first character file is obtained by the sequence compression module 114 and saved in the compression data 120.

At block 506, an intermediate file is obtained from the modified genomic data. The most-frequent character identified from the modified genomic data is removed from the modified genomic data to obtain the intermediate file having only the second most-frequent character and the least-frequent characters.

At block 508, a second character file is obtained from the intermediate file based on the current most-frequent character, i.e., second most-frequent character of the modified genomic data. In one implementation, the sequence compression module 114 analyzes the intermediate file to determine the absolute positions of the current most-frequent character. A delta difference between adjacent positions of the current most-frequent character is subsequently computed to generate the second character file. In one implementation, the delta differences thus computed are unary coded to obtain the second character file.

At block 510, the first character file and the second character file are identified as one or more most-frequent character files. In one implementation, the sequence compression module 114 identifies and saves the first character file and the second character file as the most-frequent character files in the compression data 120.

Referring to FIG. 5b, the method 308 generates one or more most-frequent character files for compressing the modified genomic data, in accordance with an embodiment of the present subject matter.

At block 512, frequency of occurrence of each of a plurality of primary characters present in the modified genomic data is computed, for example, by the sequence compression module 114. The modified genomic data is initially analyzed to compute the frequency of occurrence of each of the primary characters. Based on the computation, the primary character having the highest frequency of occurrence may be identified as a most-frequent character and the primary character having the second highest frequency of occurrence may be identified as a second most-frequent character.

At block 514, a positions file is generated based on the most-frequent character and the second most-frequent character. In one implementation, the sequence compression module 114 analyzes the modified genomic data to determine the absolute positions of the most-frequent character and the second most-frequent character. A delta difference between these adjacent positions is subsequently computed to generate the positions file. In one implementation, the delta differences thus computed are unary coded in the positions file.

At block 516, an occurrence file is obtained from the modified file. In one implementation, the modified genomic data and the positions file are analyzed to determine order of occurrence of the most-frequent character and the second most-frequent character. Based on the order of occurrence, the occurrence file is obtained, for example, by the sequence compression module 114. In one embodiment, the occurrence file is a binary file and includes the order of occurrence of the most-frequent character and the second most-frequent character in the modified genomic data in a binary format.

At block 518, the positions file and the occurrence file are identified as one or more most-frequent character files. In one implementation, the sequence compression module 114 identifies and saves the positions file and the occurrence file as the most-frequent character files in the compression data 120.

Although embodiments for compression of genomic data have been described in language specific to structural features and/or methods, it is to be understood that the invention is not necessarily limited to the specific features or methods described. Rather, the specific features and methods are disclosed as exemplary embodiments for the compression of genomic data.

We claim:

1. A computer-implemented method for compression of genomic data comprising:
    modifying, by a processor, the genomic data by removing intermediary data included in the genomic data to obtain modified genomic data, wherein the intermediary data includes all information in the genomic data apart from a plurality of primary characters, and wherein the modified genomic data includes the plurality of primary characters, wherein the genomic data is generated by sequencing genetic material obtained from one of a biological and an environmental sample;
    generating, by the processor, from the modified genomic data, one or more most-frequent character files based at least on a most-frequent character and a second most-frequent character from the plurality of primary characters, wherein the most-frequent character is a primary character, from amongst the plurality of primary characters, that occurs most frequently in the modified genomic data, and wherein the second most-frequent character is a primary character, from amongst the plurality of primary characters, that occurs second most frequently in the modified genomic data;
    creating, by the processor, a least-frequent characters file by removing the most-frequent character and the second most-frequent character from the modified genomic data; and
    producing, by the processor, compressed genomic data using at least one of the least-frequent characters file, the one or more most-frequent character files, and the intermediary data.

2. The computer-implemented method as claimed in claim 1, wherein the modifying further comprises:
    identifying header information associated with each of a plurality of genomic sequences present in the genomic data;
    identifying a length of each of the plurality of genomic sequences; and
    generating a header file having the header information and the length of each of the plurality of genomic sequences.

3. The computer-implemented method as claimed in claim 1, wherein the modifying further comprises:
    identifying one or more stretches of lower case characters in the genomic data;

computing a first delta difference between start and end positions of each of the one or more stretches to determine a length of each of the one or more stretches;

calculating a second delta difference between end position of a preceding stretch and start position of a following stretch from the one or more stretches to determine a difference in positions of the consecutive stretches; and creating a lower case character file having the first delta difference and the second delta difference.

4. The computer-implemented method as claimed in claim 1, wherein the modifying further comprises:

identifying one or more secondary characters in the genomic data;

computing a delta difference between adjacent positions of each of the one or more secondary characters; and obtaining a secondary character file having the one or more secondary characters and the corresponding delta differences.

5. The computer-implemented method as claimed in claim 1, wherein the generating comprises:

computing a frequency of occurrence of each of the plurality of primary characters to identify the most-frequent character and the second most-frequent character in the modified genomic data;

generating a first character file having delta differences between successive absolute positions of the most-frequent character in the modified genomic data, wherein the first character file is generated in a unary coded format;

removing the most-frequent character from the modified genomic data to obtain an intermediate file; and obtaining a second character file having delta differences between absolute positions of the second most-frequent character in the intermediate file, wherein the second character file is obtained in a unary coded format.

6. The computer-implemented method as claimed in claim 1, wherein the generating comprises:

computing a frequency of occurrence of each of the plurality of primary characters to identify the most-frequent character and the second most-frequent character in the modified genomic data;

obtaining absolute positions of the most-frequent character and the second most-frequent character in the modified genomic data;

encoding a delta difference between the successive absolute positions in a unary coded format to generate a positions file; and determining an order of occurrence of the most-frequent character and the second most-frequent character in the modified genomic data to obtain an occurrence file, wherein the occurrence file is generated in a binary encoded format.

7. The computer-implemented method as claimed in claim 1, wherein the least-frequent characters file is created in a binary encoded format.

8. A genomic data compression system, the system comprising:

a processor; and a memory coupled to the processor, the memory comprising:

a sequence modification module configured to modify genomic data, by removing intermediary data included in the genomic data, to obtain modified genomic data, wherein the intermediary data includes all information in the genomic data apart from a plurality of primary characters, and wherein the modified genomic data includes the plurality of primary characters, and wherein the genomic data is generated by sequencing genetic material obtained from one of a biological and an environmental sample; and a sequence compression module configured to:

generate a least-frequent characters file and one or more most-frequent character files based at least in part on the frequency of occurrence of each of the plurality of primary characters; and produce compressed genomic data having at least one of the least-frequent characters file, the one or more most-frequent character files, and the intermediary data.

9. The genomic data compression system as claimed in claim 8, wherein the sequence modification module is configured to:

generate a header file having header information and length corresponding to each of a plurality of genomic sequences present in the genomic data;

obtain a lower case character file having delta differences between start and end positions of each of one or more stretches of lower case characters in the genomic data; and produce a secondary character file having one or more secondary characters and corresponding delta differences between adjacent positions of each of the one or more secondary characters present in the genomic data.

10. The genomic data compression system as claimed in claim 9, wherein the sequence modification module is further configured to:

compute a first delta difference between start and end positions of each of the one or more stretches of lower case characters to determine length of each of the one or more stretches;

calculate a second delta difference between end and start positions of consecutive stretches of lower case characters from the one or more stretches of lower case characters to determine difference in positions of the consecutive stretches; and create the lower case character file having the first delta difference and the second delta difference.

11. The genomic data compression system as claimed in claim 8, wherein the sequence compression module is configured to:

compute a frequency of occurrence of each of the plurality of primary characters to identify a most-frequent character, a second most-frequent character, and one or more least-frequent characters in the modified genomic data; and remove the most-frequent character and the second most-frequent character from the modified genomic data to obtain the least-frequent characters file in a binary encoded format.

12. The genomic data compression system as claimed in claim 11, wherein the sequence compression module is further configured to:

generate a first character file by unary encoding a delta difference between absolute positions of the most-frequent character in the modified genomic data;

remove the most-frequent character from the modified genomic data to obtain an intermediate file;

obtain a second character file by unary encoding a delta difference between absolute positions of the second most-frequent character in the intermediate file; and identify the first character file and the second character file as the one or more most-frequent character files.

13. The genomic data compression system as claimed in claim 11, wherein the sequence compression module is further configured to obtain absolute positions of the most-frequent character and the second most-frequent character in the modified genomic data;

encode a delta difference between successive absolute positions in a unary coded format to generate a positions file;

generate, in a binary encoded format, an occurrence file based on an order of occurrence of the most-frequent character and the second most-frequent character in the modified genomic data; and identify the positions file and the occurrence file as the one or more most-frequent character files.

14. A non-transitory computer-readable medium having embodied thereon a computer program for executing a method comprising:

obtaining modified genomic data from genomic data by removing intermediary data identified from the genomic data, wherein the intermediary data includes all information in the genomic data apart from a plurality of primary characters, and wherein the modified genomic data includes the plurality of primary characters, and wherein the genomic data is generated by sequencing genetic material obtained from one of a biological and an environmental sample;

generating, from the modified genomic data, one or more most-frequent character files based at least on a most-frequent character and a second most-frequent character from among the plurality of primary characters, wherein the most-frequent character is a primary character, from amongst the plurality of primary characters, that occurs most frequently in the modified genomic data; and wherein the second most-frequent character is a primary character, from amongst the plurality of primary characters, that occurs second most frequently in the modified genomic data;

creating a least-frequent characters file by removing the most-frequent character and the second most-frequent character from the modified genomic data; and producing compressed genomic data using at least one of the least-frequent characters file, the one or more most-frequent character files, and the intermediary data.

15. The non-transitory computer readable medium as claimed in claim 14, wherein the modifying further comprises:

identifying header information associated with each of a plurality of genomic sequences present in the genomic data;

identifying a length of each of the plurality of genomic sequences; and generating a header file having the header information and the length of each of the plurality of genomic sequences.

16. The non-transitory computer readable medium as claimed in claim 14, wherein the modifying further comprises:

identifying one or more stretches of lower case characters in the genomic data;

computing a first delta difference between start and end positions of each of the one or more stretches to determine a length of each of the one or more stretches;

calculating a second delta difference between end position of a preceding stretch and start position of a following stretch from the one or more stretches to determine a difference in positions of the consecutive stretches; and creating a lower case character file having the first delta difference and the second delta difference.

17. The non-transitory computer readable medium as claimed in claim 14, wherein the modifying further comprises:

identifying one or more secondary characters in the genomic data;

computing a delta difference between adjacent positions of each of the one or more secondary characters; and obtaining a secondary character file having the one or more secondary characters and the corresponding delta differences.

18. The non-transitory computer readable medium as claimed in claim 14, wherein the generating comprises:

computing frequency of occurrence of each of the plurality of primary characters to identify the most-frequent character and the second most-frequent character in the modified genomic data;

generating a first character file having delta differences between successive absolute positions of the most-frequent character in the modified genomic data, wherein the first character file is generated in a unary coded format;

removing the most-frequent character from the modified genomic data to obtain an intermediate file; and obtaining a second character file having delta differences between absolute positions of the second most-frequent character in the intermediate file, wherein the second character file is obtained in a unary coded format.

\* \* \* \* \*

SEQUENCE LISTING

```
<160> NUMBER OF SEQ ID NOS: 7

<210> SEQ ID NO 1
<211> LENGTH: 549
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (6)..(20)
<223> OTHER INFORMATION: n may be a secondary character
<220> FEATURE:
<221> NAME/KEY: misc_feature
<222> LOCATION: (22)..(22)
<223> OTHER INFORMATION: n may be a secondary character
<220> FEATURE:
<221> NAME/KEY: misc_feature
<222> LOCATION: (35)..(35)
<223> OTHER INFORMATION: n may be a secondary character
<220> FEATURE:
<221> NAME/KEY: misc_feature
<222> LOCATION: (47)..(47)
```

<223> OTHER INFORMATION: n may be a secondary character
<220> FEATURE:
<221> NAME/KEY: misc_feature
<222> LOCATION: (51)..(51)
<223> OTHER INFORMATION: n may be a secondary character

<400> SEQUENCE: 1

```
tggggnnnnn nnnnnnnnnn anacggggtt gcggntacga cggcagngca ntgtatacga    60
ctcactatag gcgaattgg gcctctagat gcatgctcga gcggccgcca gtgtgatgga    120
tatctgcaga attcgccctt ggggttcata caccagccgg gcgacgatct ggccgtgttc   180
cagcaggaag ggggtgtcgt gggtgcggac ctccagcacg cccttggagc ccgcgccatg   240
cgcttcgtcc gtgccgaagc cggggtcgaa gaagccggcg tagtggacgc ggaactcgcc   300
cacagacggg tcgatggggg tcatttcggc ggcctgatcg accggatct  ccacgtcgtc   360 ggacgaggcc aggatgtaga actcgcccgg atccaagagc agctcgccac gacgtaggct   420
cagcggctcc cagaagtcgc gcggatcgtg gccgtcgata tggtccagat cgaccacccc   480
ggcatggcgg cggccgcgga agccgccca  aacaatacag ccgaaagcta agtgtaagcg   540
cggggtgag                                                          549
```

<210> SEQ ID NO 2
<211> LENGTH: 617
<212> TYPE: DNA
<213> ORGANISM: Unknown
<220> FEATURE:
<223> OTHER INFORMATION: Unknown genomic sequence

<400> SEQUENCE: 2

```
cccctttcagc aggatgtata gactcctata gggcgaattg ggccctctag atgcatgctc   60
gagcggccgc cagtgtgatg gatatctgca gaattcgccc ttcctcgcta tccatttggt  120
catggtctca gctacacaac gttcaagtac tcagatctca agatcaaatc tcagggtatc  180
gaggccggac cagcgactgg gcacgcgttt ggtgggacgc cgtttgatat cggagcgggc  240
attgtggtgg ctgcaatgta ttagattatg acaagatgct cttcctggcc agagaaacgc  300
agcaagctcg ttgtcatcag agaaccaaag ctttgatatc tacgtcttta tactctccaa  360
tctcggcgca gcggacatca agcgcctttc gaccattaac agtgggaaga tacccaaggt  420 accccctctct tcttcacatc ctgtggtttg tgtatggctg tcgcttgacg gcgcagctcg   480
aaccctgcat gccacgcatg cggagtattg cctgcgtcat ggtgtcacaa agggcgaatt   540
tcagcacact ggcggtcgtt actagggaat ccgagcttcg taccaggctg atgcatagct   600
tgagtattct atagtgt                                                 617
```

<210> SEQ ID NO 3
<211> LENGTH: 881
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (80)..(92)
<223> OTHER INFORMATION: n may be a secondary character
<220> FEATURE:
<221> NAME/KEY: misc_feature
<222> LOCATION: (94)..(94)
<223> OTHER INFORMATION: n may be a secondary character
<220> FEATURE:
<221> NAME/KEY: misc_feature
<222> LOCATION: (245)..(245)
<223> OTHER INFORMATION: n may be a secondary character

<400> SEQUENCE: 3

```
gaaagcaata aagaaaaaaa aaaaaaaaaa aaaaaaaaaa aaaaaaaaaa        60
aaaaaaaaaa aaatgcccan nnnnnnnnnn nncngagagc ggcgccaagc ataggtgaat   120
atagaattca gctatgcatc agcttggtac cgagctcgga tccactagta acggccgcca   180
gtgtgctgga attcgccctt gacgcaggcc gccaactacg ccaagtcggg tcgtccgacg   240
cgcgntctga tcgtcggcta caccgacacc tcgggttcgg ccgcctataa cctgggtctg   300
tccaaccgtc gttcgcgcac cgtcgcggac gccctggtgg ctcaaggcgt caacggcggc   360
gtgatcgccc tggacggcaa gggcgaaacc aacctggcca agcccaccgc cgacggcgtg   420
cgtgaaccgc tcaaccgccg cgcgaccatc gacatcaact tctaagaccc aatggaaagc   480
cggtctggac aaccagaccg gcgatcctga ggatcagatg tcgaacgact ttgacgccgt   540
ctccgaaagg gggcggcgtt tctgtttgcg tagaagggtc agtcttgagc ggtgacggtc   600
aacggcgggc ttggcgcgct gaacgattgt cggcttagaa ccgcctcgcc aagcgcgatc   660
accacggtcg ccgtcagaag ggcgcagacc accgcgacgg cggccagctt caggccttgt   720
ccaaaatccc agtcgtccgg cgtcacggcg tcgctcctgc ggagggcttt gctcggccta   780
accccgatgt tcgacatccc gcaagcgcga ccggcgggca gggatgcgaa aagggcgacg   840
tcttgcgacg ccgccccgat gatctttccc tgatgtcgat c                     881
```

<210> SEQ ID NO 4
<211> LENGTH: 2008
<212> TYPE: DNA
<213> ORGANISM: Unknown
<220> FEATURE:
<223> OTHER INFORMATION: Unknown genomic sequence

<400> SEQUENCE: 4

```
tggggaacgg ggttgcggta cgacggcagg catgtatacg actcactata gggcgaattg    60
ggcctctaga tgcatgctcg agcggccgcc agtgtgatgg atatctgcag aattcgccct   120
tggggttcat acaccagccg ggcgacgatc tggccgtgtt ccagcaggaa gggggtgtcg   180
tgggtgcgga cctccagcac gcccttggag cccgcgccat gcgcttcgtc cgtgccgaag   240
ccggggtcga agaagccggc gtagtggacg cggaactcgc ccacagacgg gtcgatgggg   300
gtcatttcgg cggcctgatc gaccgggatc tccacgtcgt cggacgaggc caggatgtag   360
aactcgcccg gatccaagag cagctcgcca cgacgtaggc tcagcggctc ccagaagtcg   420
cgcggatcgt ggccgtcgat atggtccaga tcgaccaccc cggcatggcg gcggccgcgg   480
aagccgcccc aaacaataca gccgaaagct aagtgtaagc gcggggtgag ccccttcagc   540
aggatgtata gactcctata gggcgaattg ggccctctag atgcatgctc gagcggccgc   600
cagtgtgatg gatatctgca gaattcgccc ttcctcgcta tccatttggt catggtctca   660
gctacacaac gttcaagtac tcagatctca agatcaaatc tcagggtatc gaggccggac   720
cagcgactgg gcacgcgttt ggtgggacgc cgtttgatat cggagcgggc attgtggtgg   780
ctgcaatgta ttagattatg acaagatgct cttcctggcc agagaaacgc agcaagctcg   840
ttgtcatcag agaaccaaag ctttgatatc tacgtcttta tactctccaa tctcggcgca   900
gcggacatca agcgcctttc gaccattaac agtgggaaga tacccaaggt acccctctct   960
tcttcacatc ctgtggtttg tgtatggctg tcgcttgacg gcgcagctcg aaccctgcat  1020
gccacgcatg cggagtattg cctgcgtcat ggtgtcacaa agggcgaatt tcagcacact  1080
```

| | | |
|---|---|---|
| ggcggtcgtt actagggaat ccgagcttcg taccaggctg atgcatagct tgagtattct | 1140 | |
| atagtgtgaa agcaataaag aaaaaaaaaa aaaaaaaaa aaaaaaaaaa aaaaaaaaaa | 1200 | |
| aaaaaaaaaa aaaaaaaaaa cgagagcggc gccaagcata ggtgaatata gaatatcagc | 1260 | |
| tatgcatcag cttggtaccg agctcggatc cactagtaac ggccgccagt gtgctggaat | 1320 | |
| tcgcccttga cgcaggccgc caactacgcc aagtcgggtc gtccgacgcg cgtctgatcg | 1380 | |
| tcggctacac cgacacctcg ggttcggccg cctataacct gggtctgtcc aaccgtcgtt | 1440 | |
| cgcgcaccgt cgcggacgcc ctggtggctc aaggcgtcaa cggcggcgtg atcgccctgg | 1500 | |
| acggcaaggg cgaaaccaac ctggccaagc ccaccgccga cggcgtgcgt gaaccgctca | 1560 | |
| accgccgcgc gaccatcgac atcaacttct aagacccaat ggaaagccgg tctggacaac | 1620 | |
| cagaccggcg atcctgagga tcagatgtcg aacgactttg acgccgtctc cgaaaggggg | 1680 | |
| cggcgtttct gtttgcgtag aagggtcagt cttgagcggt gacggtcaac ggcgggcttg | 1740 | |
| gcgcgctgaa cgattgtcgg cttagaaccg cctcgccaag cgcgatcacc acggtcgccg | 1800 | |
| tcagaagggc gcagaccacc gcgacggcgg ccagcttcag gccttgtcca aaatcccagt | 1860 | |
| cgtccggcgt cacggcgtcg ctcctgcgga gggctttgct cggcctaacc ccgatgttcg | 1920 | |
| acatcccgca agcgcgaccg gcgggcaggg atgcgaaaag ggcgacgtct tgcgacgccg | 1980 | |
| ccccgatgat ctttccctga tgtcgatc | 2008 | |

<210> SEQ ID NO 5
<211> LENGTH: 841
<212> TYPE: DNA
<213> ORGANISM: Unknown
<220> FEATURE:
<223> OTHER INFORMATION: Unknown genomic sequence

<400> SEQUENCE: 5

| | | |
|---|---|---|
| taatttaaaa ttataatata taaattttaa tattaattat atattaaatt ttttataaaa | 60 | |
| attttttaaaa ttttataatt aatttttaat aaaatataaa taatatttat tttataatta | 120 | |
| ttaaaattaa atataaaata atatataaat atttatatta ataaataaaa aaataaaaat | 180 | |
| aattaatatt aaattataat tataaatttt aatattaatt atatattaaa ttttttatat | 240 | |
| tttatttata aaattaatat aattaaataa attatataaa atattttatt tatataattt | 300 | |
| ttaattatta attataaaat ttttaaaaaa aattttataa aaaaatttat attatttttat | 360 | |
| attaattaaa taatttaatt aaataaataa atatttttta attttttta tttttaataa | 420 | |
| tataatatat tttatttaaa aaatttaaat tttataaata tttaatatat attatattta | 480 | |
| tattaaaaat aaaaaaaaaa aaaaaaaaaa aaaaaaaaaa aaaaaaaaaa aaaaaaaaaa | 540 | |
| aaaaaaaaaa aaaaaaaata taatataaat atatatatat ttaatatata taaatttaat | 600 | |
| tttaaaataa atttattatt taaaattta taattttaat ttatatttaa taatattaaa | 660 | |
| aaaaataaaa ttaataaaat aataatttaa aaataaatta aaaattaat aattaaattt | 720 | |
| attaaatttt tttaaaatat ttatataatt taaattttta ataaataat taaaaaaaat | 780 | |
| tatttaaaat atttatttat ttttaaattt aataaaaata aaaatttaat attttttatta | 840 | |
| t | 841 | |

<210> SEQ ID NO 6
<211> LENGTH: 227
<212> TYPE: DNA
<213> ORGANISM: Unknown
<220> FEATURE:
<223> OTHER INFORMATION: Unknown genomic sequence -continued

```
<400> SEQUENCE: 6
cgccgcccgg ggggcggcgc ggcggggggcg cggcgggcgg ccggcgggcg gcgcgcgcgg      60
cggcgccgcc cgccgcgcgc cccggcgccg cggggcgcgc cccgcgcggc ggccgccggc     120 cgccccgcg  ccggcgccgg cgcgcccgcg ggggcgccgg ccccccggcg ccccgcgcgc     180
gccggcgggc ggggcggggc gcgcgcgcgc cgccccggcc ccggcgc                   227

<210> SEQ ID NO 7
<211> LENGTH: 841
<212> TYPE: DNA
<213> ORGANISM: Unknown
<220> FEATURE:
<223> OTHER INFORMATION: Unknown genomic sequence

<400> SEQUENCE: 7
taatttaaaa ttataatata taaatttta  tattaattat atattaaatt ttttataaaa      60
atttttaaaa ttttataatt aatttttaat aaaatataaa taatatttat tttataatta    120
ttaaaattaa atataaaata atatataaat atttatatta ataaataaaa aaataaaaat    180
aattaatatt aaattataat tataaattt  aatattaatt atatattaaa tttttttatat    240 tttatttata aaattaatat aattaaataa attatataaa atattttatt tatataattt    300
ttaattatta attataaaat ttttaaaaaa aattttataa aaaaatttat attattttat    360
attaattaaa taatttaatt aaataaataa atatttttta atttttttta tttttaataa    420
tataatatat tttatttaaa aaatttaaat tttataaata tttaatatat attatattta    480
tattaaaaat aaaaaaaaaa aaaaaaaaaa aaaaaaaaa  aaaaaaaaaa aaaaaaaaaa    540
aaaaaaaaaa aaaaaaaata taatataaat atatatatat ttaatatata taaatttaat    600
tttaaaataa atttattatt taaaatttta taattttaat ttatatttaa taatattaaa    660
aaaaataaaa ttaataaaat aataatttaa aaataaatta aaaaattaat aattaaattt    720
attaaatttt ttttaaatat ttatataatt taaattttta aataaataat taaaaaaaat    780
tatttaaaat atttatttat ttttaaattt aataaaaata aaaatttaat atttttatta    840
t                                                                    841
```